(12) United States Patent
Bian et al.

(10) Patent No.: US 9,889,086 B2
(45) Date of Patent: Feb. 13, 2018

(54) BIOADHESIVE AND INJECTABLE HYDROGEL

(71) Applicant: The Chinese University of Hong Kong, Shatin, N.T., Hong Kong (CN)

(72) Inventors: Liming Bian, Hong Kong (CN); Qian Feng, Hong Kong (CN); Kongchang Wei, Hong Kong (CN); Gang Li, Hong Kong (CN); Sien Lin, Hong Kong (CN)

(73) Assignee: The Chinese University of Hong Kong, Shatin, N.T., Hong Kong (CN)

( * ) Notice: Subject to any disclaimer, the term of this patent is extended or adjusted under 35 U.S.C. 154(b) by 11 days.

(21) Appl. No.: 15/013,657

(22) Filed: Feb. 2, 2016

(65) Prior Publication Data
US 2016/0237225 A1 Aug. 18, 2016

Related U.S. Application Data

(60) Provisional application No. 62/115,511, filed on Feb. 12, 2015.

(51) Int. Cl.
| | |
|---|---|
| A61K 47/40 | (2006.01) |
| A61K 47/42 | (2017.01) |
| A61K 9/00 | (2006.01) |
| A61L 26/00 | (2006.01) |
| A61L 27/22 | (2006.01) |
| A61L 27/52 | (2006.01) |
| C08F 289/00 | (2006.01) |
| A61L 27/54 | (2006.01) |
| A61K 47/32 | (2006.01) |

(52) U.S. Cl.
CPC ............ *A61K 9/0019* (2013.01); *A61K 47/32* (2013.01); *A61K 47/40* (2013.01); *A61K 47/42* (2013.01); *A61L 26/008* (2013.01); *A61L 26/0038* (2013.01); *A61L 26/0066* (2013.01); *A61L 27/222* (2013.01); *A61L 27/52* (2013.01); *A61L 27/54* (2013.01); *C08F 289/00* (2013.01); *A61L 2300/64* (2013.01); *A61L 2400/06* (2013.01)

(58) Field of Classification Search
CPC ......... A61K 47/40; A61K 47/32; A61K 47/42
See application file for complete search history.

(56) References Cited

PUBLICATIONS

Hou et al., "A kind of novel biodegradable hydrogel made from copolymerization of gelatin with polypseudoaxanes based on α-CDs", Biomed Mater. 2, 2007, S147-S152.*
Wang et al., "Polymeric networks assembled by adamantly and B-cyclodextrin substituted poly(acrylate)s: Host-guest interactions, and the effects of ionic strength and extent of substitution", Ind. Eng. Chem. Res. 2010, 49, 609-612.*
Wu et al. "Fabrication of supramolecular hydrogels for drug delivery and stem cell encapsulation", Langmuir, 2008, vol. 24, No. 18, pp. 10306-10312.*

* cited by examiner

*Primary Examiner* — Gina Justice
(74) *Attorney, Agent, or Firm* — Kilpatrick Townsend & Stockton LLP

(57) ABSTRACT

The present invention provides a novel hydrogel, methods of its use, and methods for producing the hydrogel.

24 Claims, 20 Drawing Sheets

BIOADHESIVE AND INJECTABLE HYDROGEL

RELATED APPLICATIONS

This application claims priority to U.S. Provisional Patent Application No. 62/112,511, filed Feb. 5, 2015, the contents of which are hereby incorporated by reference in the entirety for all purposes.

BACKGROUND OF THE INVENTION

Typical hydrogels are gel-like or colloidal substances made of water and solids. They are often created chemically through a combination of ultra violet cross-linking and chemical interface. Hydrogels have a broad range of applications in the biomedical field such as tissue engineering and drug delivery. For instance, they can be used as biomaterial carriers in transdermal drug delivery, wound care, conductive and non-conductive adhesives, cosmetic patches and masks, components for medical devices, temperature management, medical diagnostics, and the like.

Despite their wide used in biomedical applications, conventional hydrogels have some drawbacks: they are often weak in mechanical property, incapable of self-healing after fragmentation, difficult to inject, unable to conform to irregular geometry, and unable to deliver non-water soluble drugs. As such, there remains a need to develop new and improved hydrogels. The present invention addresses this and other related needs.

BRIEF SUMMARY OF THE INVENTION

This invention provides new supramolecular hydrogels as well as methods for making and using the hydrogels. The exemplary new hydrogels made by the present inventors exhibit the following advantages: gelatin used in the hydrogels is not chemically modified and therefore provides better biocompatibility than the chemically modified gelatin, which is typically used in many conventional hydrogels. The new hydrogels are mechanically robust and can sustain repeated excessive tension or compression with reduced likelihood to fragment. The new hydrogels are capable of self-healing and thus capable of reintegration after mechanical disruption, resulting in enhanced retention after injection at the targeted sites. The new hydrogels are injectable in the gelation form, easy to use, and can be prepared first and used at a prescribed time later, eliminating the need to prepare precursor solutions immediately before injection as often required in the use of conventional hydrogels. The new hydrogels are adhesive to soft tissues under aqueous condition, providing good retention after injection at the targeted sites and less loss to the unwanted areas. The new hydrogels are also permissive to cell infiltration and migration, thus facilitating recruitment of the endogenous cells to speed up the healing of the injured tissues at the injected sites. Furthermore, the new hydrogels are (1) capable for the delivery of cells; (2) capable for the delivery of non-water soluble drugs; and (3) conducive to the differentiations of the carried stem cells, all of which can help with speeding up the healing of the injured tissues at the sites where the hydrogels are injected.

Thus, in one aspect, the present invention provides a method of producing a novel hydrogel. The method comprises these steps: the first step is complexing a host molecule and a guest molecule, wherein the host molecule presents a pocket (such as a hydrophobic pocket) that can accommodate and form a physical interaction with a guest molecule or a side group of the guest molecule (such as a benzene ring). Typically the complexing is based on a physical interaction. At least one of the host molecule and the guest molecule comprises a monomer component. Second step is polymerizing the monomer components to form a cross-linked mesh of the host molecules and guest molecules.

In some embodiments, the host molecule is an acrylated β-cyclodextrin. In some embodiments, the host molecule has a monomer component, such as an acrylate. In some embodiments, the guest molecule is a gelatin. In some embodiments, the polymerization is initiated by UV radiation. In some embodiments, the host molecule and the guest molecule are placed in an aqueous solution together. In some embodiments, at least one additional molecule is present in the first step when the host molecule and the guest molecule are complexed: for example, the at least one additional molecule is a pharmaceutically active ingredient. In some embodiments, the host molecule is a mono-acrylated β-cyclodextrin and the guest molecule is a gelatin.

In a second aspect, the present invention provides a novel hydrogel. The hydrogel comprises a cross-linked mesh of a host molecule and a guest molecule in accordance with the description above: the host molecule presents a structural pocket (e.g., a hydrophobic pocket) that accommodates a side group of a guest molecule (such as a benzene ring) or a guest molecule itself. The host molecule and guest molecule form a physical interaction between the pocket and the side group/guest molecule. At least one of the host and guest molecules further comprises a monomer component, and the monomer components are polymerized to form the cross-linked mesh, typically after the complexing of the host and guest molecules. In some cases, the hydrogel is produced by way of the method described above, i.e., by the sequential steps of first complexing a host molecule with a guest molecule and then polymerization of the monomer components.

In some embodiments, the host molecule is an acrylated β-cyclodextrin. In some embodiments, the guest molecule is a gelatin. In some embodiments, the monomer component is an acrylate. In some embodiments, the host molecule is a mono-acrylated β-cyclodextrin and the guest molecule is a gelatin. In some embodiments, the hydrogel is formulated in an injectable form. In some embodiments, the hydrogel further comprises at least one additional molecule, such as a pharmaceutically active ingredient. In some embodiments, the hydrogel is present in a composition that also comprises a live cell, such as a live stem cell. In a related aspect, the invention provides a kit for drug delivery, wound healing, or promoting cell growth and/or cell differentiation, which comprises the hydrogel of this invention as described herein and a pharmaceutically active ingredient and/or a live cell, such as a live stem cell.

In a third aspect, the present invention provides a method for using the hydrogel. The method comprises the step of administrating to a patient the hydrogel of this invention as described above for various purposes. For example, the hydrogel formulates to comprise a pharmaceutically active ingredient can be used for delivering of the active ingredient. As an another example, in a method for promoting cell proliferation or differentiation, a step is performed to administer to a patient the hydrogel of this invention (such as in the injectable form), e.g., applying the hydrogel to a wound site in the patient's body, such as a surgical wound immediately after a surgical procedure is performed on a patient's body.

BRIEF DESCRIPTION OF THE DRAWINGS

FIGS. 4A-4B 2D Cell culture study in vitro. 4a, confocal micrographs showing the 3D distribution of DAPI-stained hMSC nuclei within the $Gel_8$-$CD_{10}$ (left) and MeGel (right) hydrogels after 2 hours of exposure to an chemoattractant gradient (right, top and front views). 4b, alkaline phosphatase (ALP) staining and Von Kossa staining of the hMSC-seeded 2D $Gel_8$-$CD_{10}$ hydrogel substrates. No Dex: control without Dex supplementation; Dex in hydrogel: a single bolus of Dex (identical amount as used in the "Dex in media" group) is loaded in the β-CDs in the hydrogels without supplementation in media; Dex in media: Dex is supplemented to the media continuously. Scale bars, 100 μm (b) and 50 μm (inserts).

FIGS. 5A-5E 3D Cell culture study in vitro and in vivo. 5a, cell viability staining of the hMSC-laden MeGel and $Gel_8$-$CD_{10}$ hydrogels after 1 day (top) and 14 days (middle) of culture, and after 2 days of culture following injection of the HGM hydrogels (bottom). 5b, gene expression (normalized to GAPDH) of selected osteogenic markers (alkaline phosphatase (ALP), type collagen I (Col I), runt-related transcription factor 2 (Runx2), and osteocalcin (OC)) 5c, calcium content (normalized to total protein content) and 5d, hematoxylin and eosin stain (H&E) staining, von kossa staining, and type I collagen (Col I) immunohistochemical stainining of hMSC-laden HGM and MeGel hydrogels after 14 days of osteogenic culture. 5e, stereoscopic pictures, H&E staining, masson trichrome staining, and Col I immunohistochemical staining of the harvested HGM hydrogels after 14 days subcutaneous implantation in nude mice. +hMSCs, −injection: hMSC-laden HGM hydrogels directly inserted subcutaneously; +hMSCs, +injection: hMSC-laden HGM hydrogels injected subcutaneously; −hMSCs, −injection: acellular HGM hydrogels directly inserted subcutaneously; −hMSCs, +injection: acellular HGM hydrogels injected subcutaneously. All groups are loaded with Dex (same amount as that used in in vitro studies). Scale bars, 25 μm (d,e) and 500 μm (inserts) except 1 mm (e, hydrogel images). *$p<0.05$, **$p<0.001$.

FIG. 9A, time sweep of dynamic rheology study on $Gel_x$-$CD_y$. FIG. 9B, strain-stress curves of Me-gelatin and $Gel_x$-$CD_y$; FIG. 9C, cyclic tensile testing of $Gel_8$-$CD_{10}$.

DETAILED DESCRIPTION OF THE INVENTION

I. Introduction

Figure 1:
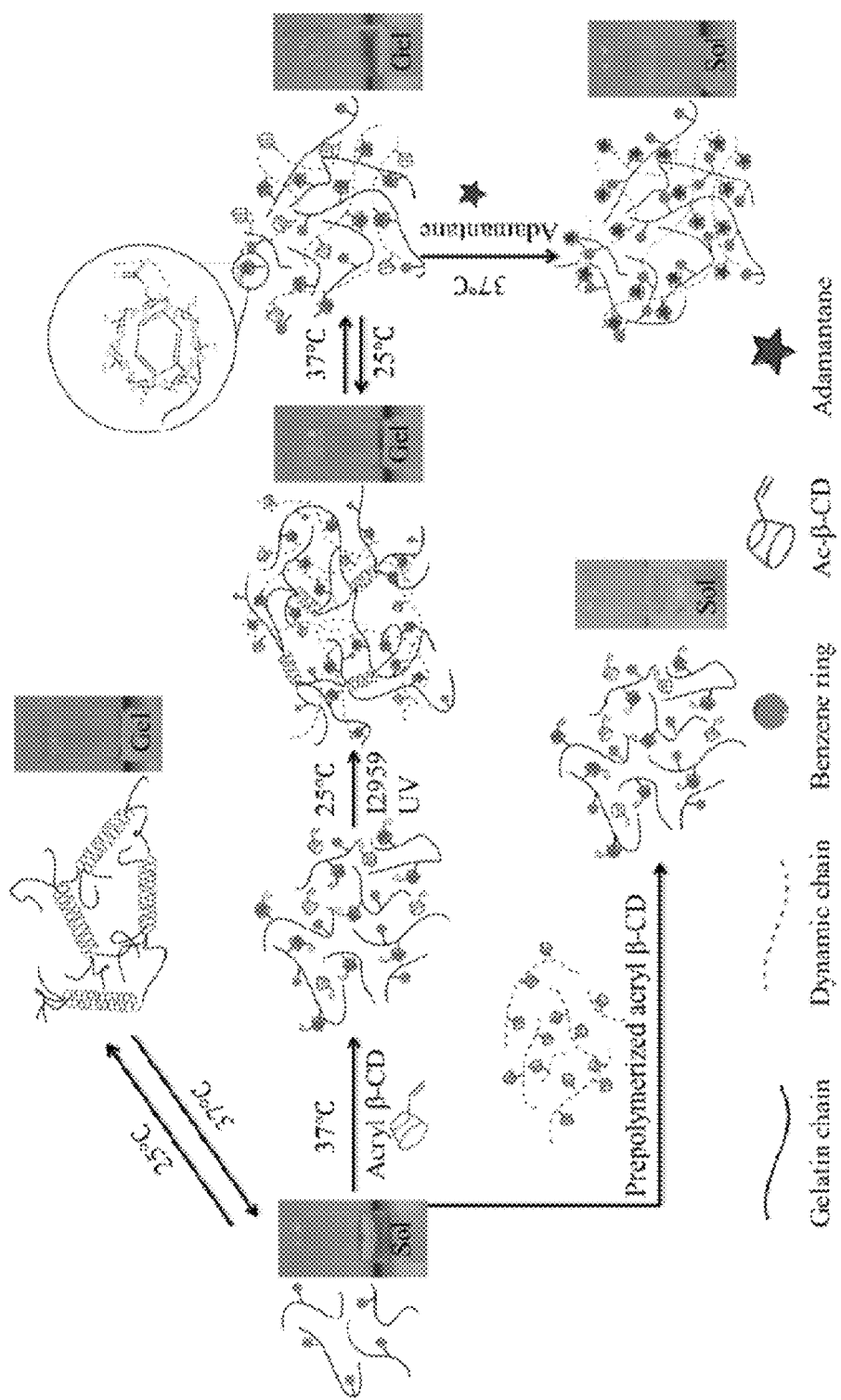
FIG. 1 Schematics of supramolecular hydrogel formation and dissolution.

The present inventors have developed a novel form of hydrogel that is mechanically resilient, biocompatible, self-healing, and injectable, which can be used to deliver therapeutic cells and non-water soluble small molecular drugs. The novelty of the hydrogel lies in three aspects. Firstly, compared to the conventional physically crosslinked hydrogels, the newly developed hydrogel possesses significantly improved mechanical properties. Secondly, the hydrogel possesses properties such as biocompatibility, self-healing, moldability, and easy injectability, which are highly desirable for biomedical applications. Lastly, the hydrogel of this invention can be used as carriers to simultaneously deliver mesenchymal stem cells and small molecule drugs. The new hydrogel can be used in minimal invasive therapies for repairing other connective tissues including cartilage, bone, ligaments, meniscus and intervertebral disc.

II. Production of Hydrogel of the Invention

A. General

A hydrogel is a network or scaffolding of natural or synthetic polymer chains that are hydrophilic, sometimes found as a colloidal gel in which water is the dispersion medium. Being polymer networks that have high waterabsorbing capacity, hydrogels often closely mimic native extracellular matrices. Hydrogels also tend to possess a degree of flexibility very similar to natural tissues, due to the relatively high water content: in some cases, hydrogels can contain well over 90% water.

Common ingredients used in hydrogels include polyvinyl alcohol, sodium polyacrylate, acrylate polymers and copolymers with an abundance of hydrophilic groups. Natural hydrogel materials are being investigated for tissue engineering; these materials include agarose, methylcellulose, hyaluronan, and other naturally derived polymers.

Since hydrogels possess some natural tissue-like features, they are frequently used for drug delivery and tissue repair. As hydrogel-based cell delivery systems are being increasingly employed in regenerative medicine, several advances have been made in the hydrogel chemistry and modification for enhanced control of cell fate and functions, and modulation of cell and tissue responses against oxidative stress and inflammation in the tissue environment. One notable drawback of currently existing hydrogels is the lack of mechanical strength. Therefore, maintaining and improving the mechanical integrity of hydrogel scaffolding becomes increasingly important for the performance of hydrogels. The present inventors have provided a novel and unique method of producing hydrogels of improved characteristics.

Briefly, the novel hydrogels of this invention comprising a cross-linked network of host molecules and guest molecules. The basis of the crosslinking is the polymerization of a monomer component of the host molecule. In addition, the host molecule and the guest molecule are complexed via a physical interaction between the two molecules, for example, between a hydrophobic pocket of the host molecule and a benzene ring of a guest molecule (e.g., from a phenylalanine residue of a protein). Other forms of physical interaction may include hydrogen bonding, electrostatic attraction, and van der Waals forces, in addition to hydrophobic effects. This unique formation of hydrogel presents various advantages including improved mechanical strength, self-healing ability, and drug delivery capacity.

B. Components and Preparation of Hydrogel of the Invention

The hydrogel of this invention is a unique composition of the so-called "Host-Guest Macromer," which comprises two main components: (1) a Host molecule; and (2) a Guest molecule. A variety of molecules can serve as the Host molecule. Structurally, the Host molecule presents a pocket-like structure to accept the Guest molecule to form a complex with the Guest molecule based on a type of physical interaction, such as hydrophobic effects, hydrogen bonding, electrostatic attraction, and van der Waals forces. For example, the Host molecule presents a hydrophobic pocket, which would accommodate a hydrophobic side group of the Guest molecule. As another example, a positively charged pocket structure presented by the Host molecule can complex with a negatively charged Guest molecule, or vice versa, by way of electrostatic attraction.

Based on a type of interaction physical in nature (as opposed to a chemical bond), such as hydrophobic effect, hydrogen bonding, electrostatic attraction, and van der Waals forces, the Host molecule and the Guest molecule can complex with each other via the hydrophobic pocket and hydrophobic side group to form the primary level of Host-Guest relationship. The Guest molecule can be any molecule so long as it presents a suitable side group that can fit into the corresponding pocket of the Host molecule. For example, the Guest molecule can be a polypeptide that presents adequate number of hydrophobic amino acids such as alanine, valine, isoleucine, leucine, methionine, phenylalanine, tyrosine, and tryptophan. In some embodiments, the hydrophobic pocket presented by a cyclodextrin (e.g., β-cyclodextrin) may complex with a hydrophobic side group presented by a polypeptide (e.g., the hydrophobic side chain of phenylalanine, tyrosine, or tryptophan, such as the benzene ring of a phenylalanine residue). Proper pairing of the Host molecule and the Guest molecule for the purpose of forming the primary level of complexing can be determined and ensured based on 3-dimensional modeling and analysis of both molecules.

In addition to the primary level of "complexing" of the Host and Guest molecules, there exists a secondary level of connection between the Host and Guest molecules. Typically, the Host molecule comprises a component that is capable of polymerization, i.e., a monomer component. After the physical complexing of the Host and Guest molecules is completed, the polymerization process is initiated so that the monomer components of the Host molecules can form a polymer chain, resulting in a network of the Host molecules and providing further structural support for the Host-Guest Macromer. A range of monomers capable of polymerization can be included in a Host molecule by chemical conjugation. One exemplary pair of Host and Guest molecules is acrylated β-cyclodextrin and gelatin, where the β-cyclodextrin molecule is functionalized by conjugation of an acrylate, which can be readily induced into polymerization, e.g., by UV radiation. Once the secondary level of connection is established, hydrogel of the Host-Guest Macromer is made.

In some cases, it is the Guest molecule rather than the Host molecule that comprises a component capable of polymerization, i.e., a monomer component, which undergoes polymerization after complex formation between the Host and Guest molecule by physical interaction is completed. In other cases, both the Host molecule and the Guest molecules include a monomer component. The monomer component of at least one of the Host and Guest molecules remains unpolymerized until after the physical complexing of the Host-Guest molecules is complete: in some cases, the monomer component of the Host molecule may have undergone polymerization prior to the physical complexing of the Host-Guest molecules, whereas the monomer component of the Guest molecule undergoes polymerization after the physical complexing of the Host-Guest molecules. In other cases, the monomer component of the Guest molecule may have undergone polymerization prior to the physical complexing of the Host-Guest molecules, whereas the monomer component of the Host molecule undergoes polymerization after the physical complexing of the Host-Guest molecules. Yet in some other cases, the monomer components of both the Host and the Guest molecules undergo polymerization after the physical complexing of the Host-Guest molecules.

Figure 11:
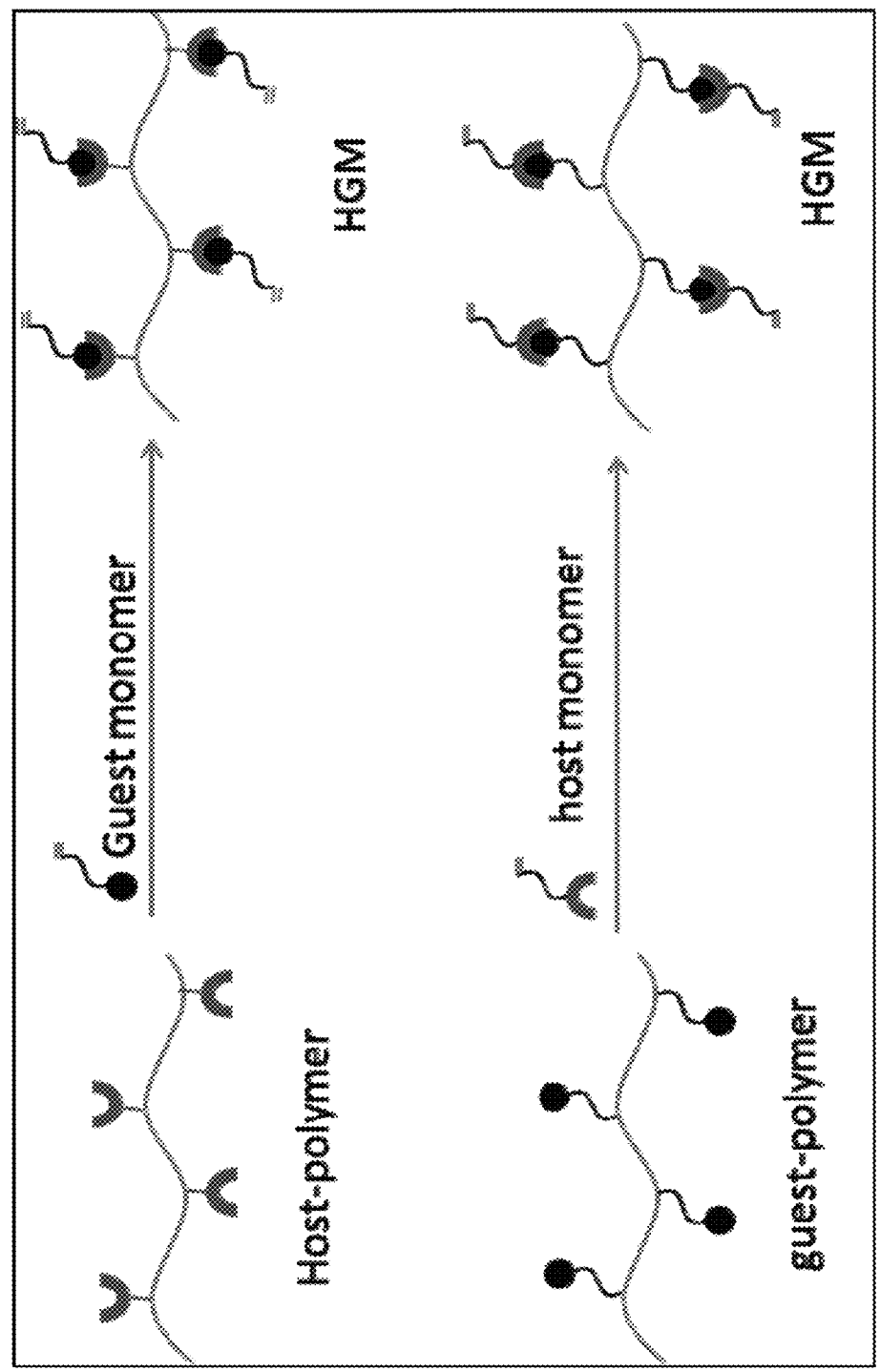
FIG. 11 Two strategies to prepare host-guest-macromer (HGM): host-polymer/guest-monomer strategy and guest-polymer/host-monomer strategy.
Figure 12:
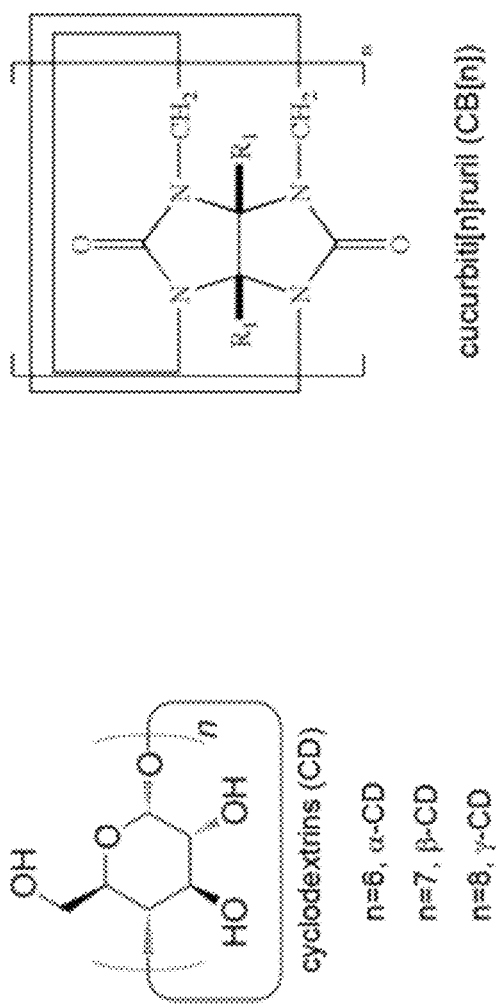
FIG. 12 The potential hosts that can be applied in the two strategies: "cyclic molecules (with n repeating units joined head to tail to form a ring like structure)" include but are not limited to cyclodextrins (CDs), cucurbituril (CB), and pillararene, as well as their derivatives with various functionalities.
Figure 12:
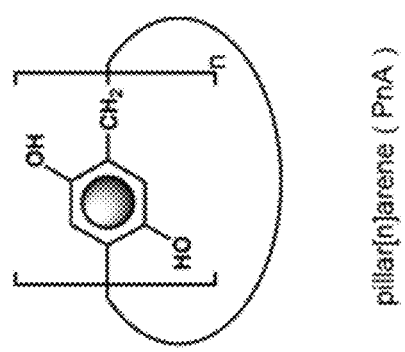
Figure 12:
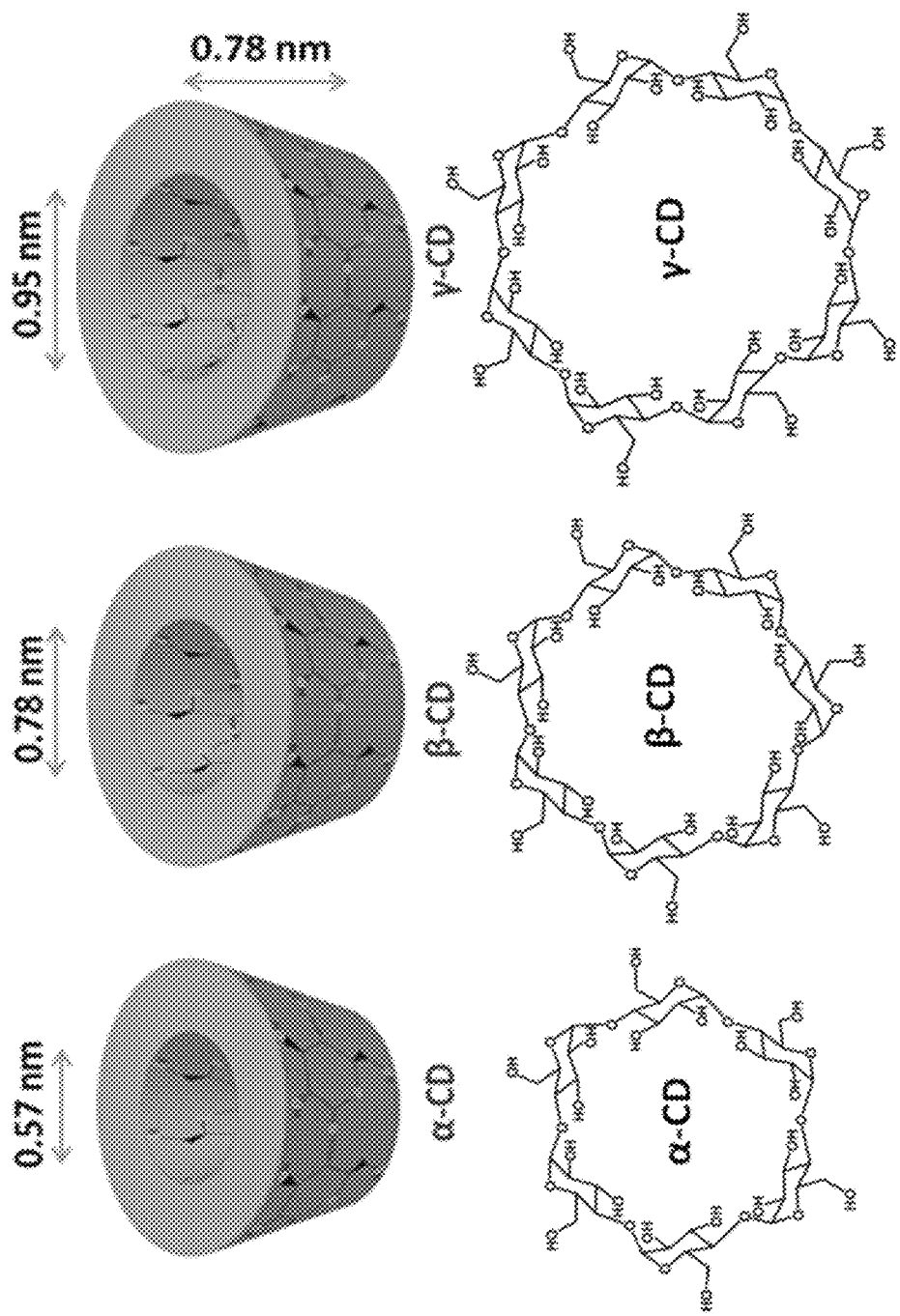
Figure 13:
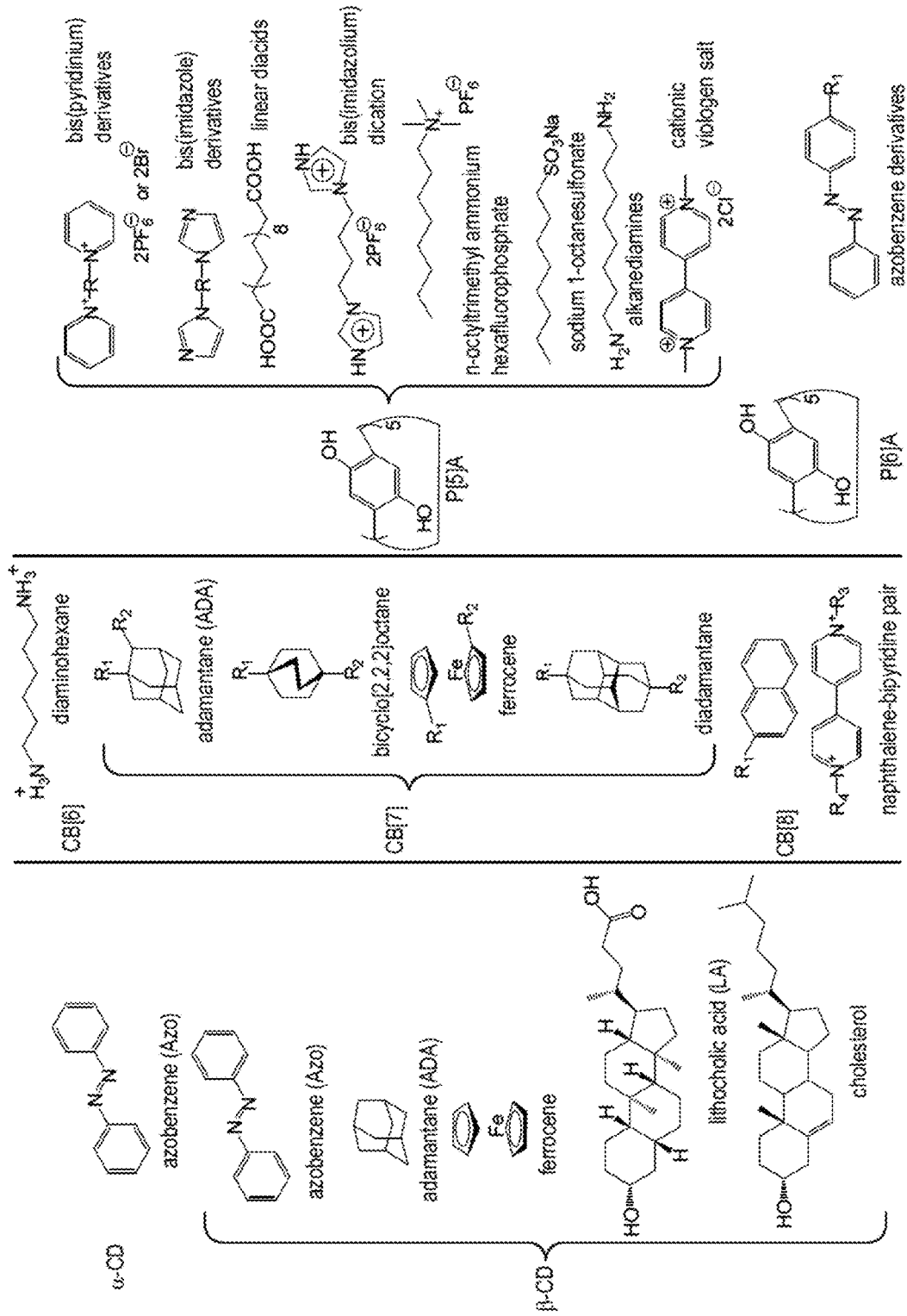
FIG. 13 Guest molecules: molecules that bind to Host molecules via non-covalent interactions (such as hydrogen bonding, hydrophobic interaction, electrostatic interaction). Exemplary guests for corresponding group of hosts are shown in this figure.

A variety of chemical/physical structures may be present in the Host-Guest molecule pairs suitable for use in practicing the present invention. Basic strategies of matching Host-Guest molecules and some examples are provided in FIGS. 11-13.

III. Use of Hydrogel of the Invention

Common uses for existing hydrogels and like materials include:

(1) Scaffolds in tissue engineering: when used as scaffolds, hydrogels may contain human cells to repair tissue;
(2) Hydrogel-coated wells have been used for cell culture;
(3) Environmentally sensitive hydrogels—also known as "Smart Gels" or "Intelligent Gels": these hydrogels have the ability to sense changes of pH, temperature, or the concentration of metabolite and release their load as result of such a change;
(4) Sustained-release drug delivery systems;
(5) Providing absorption, desloughing and debriding of necrotic and fibrotic tissue;
(6) Hydrogels that are responsive to specific molecules, such as glucose or antigens, can be used as biosensors, as well as in DDS;
(7) Disposable diapers where they absorb urine, or in sanitary napkins;
(8) Contact lenses (e.g., silicone hydrogels, polyacrylamides, polymacon);
(9) EEG and ECG medical electrodes using hydrogels composed of cross-linked polymers (polyethylene oxide, polyAMPS and polyvinylpyrrolidone);
(10) Water gel explosives;
(11) Rectal drug delivery and diagnosis; and
(12) Encapsulation of quantum dots.

Hydrogels are also known to be used as tissue implants (e.g., breast implants), glues, granules for holding soil moisture in and areas, and dressings for healing of burn or other hard-to-heal wounds. Due to their high water contents, hydrogels are excellent wound gels for helping to create or maintain a moist environment. In addition, hydrogels can be used as reservoirs in topical drug delivery, particularly ionic drugs, delivered by means of iontophoresis.

The hydrogels of this invention are capable of all of the above named uses while providing certain distinct advantages. In particular, the gelatin used in the hydrogel of this invention is not chemically modified, thus affording better biocompatibility than most of the existing hydrogel incorporating chemically modified gelatin. The hydrogel of this invention is mechanically more robust than existing hydrogels in that it can sustain repeated excessive tension or compression and is less likely to fragment in comparison. The new hydrogel can be readily formulated in an injectable form, which makes this gelatin-based material easy to use since this type of hydrogel can be prepared first and used at a later time, without the need of preparing any precursor solutions immediately before injection as often required in the use of some pre-existing hydrogels or similar materials. In a related aspect, the hydrogel of this invention possesses a remarkable self-healing capacity, which means the hydrogel is capable of reintegration after it is mechanical disrupted. This property renders the new hydrogel an enhanced retention ability after it is applied (e.g., by injection) at targeted sites.

Further, the hydrogel of this invention serves as an effective adhesive to soft tissues under aqueous condition, resulting good retention of the hydrogel after its application at the targeted anatomic sites with minimized loss or transfer to any unrelated areas in a patient's body. One significant feature of the new hydrogel is that it is highly permissive to cell infiltration and migration. This feature facilitates recruitment of endogenous cells at a relevant anatomic site where the hydrogel is application, thus shortening the time required for tissue healing at a site of injury such as a traumatic injury or a surgical wound. Also due to this important feature, the hydrogel of this invention is capable of effective delivery of cells and effective delivery of pharmaceutically active ingredients (especially non-water soluble drugs). Thus, the hydrogel of this invention is particularly useful for promoting faster healing of injuries compared existing materials for the same or equivalent uses, including promoting differentiation of live stem cells that are carried by the hydrogel for the purpose of facilitating tissue healing process.

EXAMPLES

The following examples are provided by way of illustration only and not by way of limitation. Those of skill in the art will readily recognize a variety of non-critical parameters that could be changed or modified to yield essentially the same or similar results.

Example 1

Biopolymeric hydrogels are promising injectable materials for many biomedical applications. Here the inventors provide a novel and facile supramolecular approach to prepare biopolymeric hydrogels, which is free from complex modifications and direct chemical crosslinking of biopolymers. The inventors have prepared an acrylated gelatinous "Host-Guest Macromer" (HGM) via the efficient host-guest complexation between phenylalanines of gelatin and the free diffusing photo-crosslinkable acrylated β-cyclodextrins monomer (Ac-β-CD). Subsequent photo-initiated radical polymerization of the HGM produces highly elastic, stretchable, injectable and self-healable supramolecular hydrogels that are solely stabilized by the physical host (β-CD)-guest (benzene ring of phenylalanine) complexation. The enhanced mechanical resilience and self-healing capability of the HGM supramolecular hydrogels makes them ideal carrier materials of therapeutic cells/drugs for repairing load bearing tissues. The reversible physical crosslink of the HGM hydrogels allow infiltration and migration of the cells into the hydrogels, fostering the involvement of the endogenous cells in tissue healing. The shear shining property of the HGM hydrogels potentially allows pre-operation hydrogel preparation and storage before facile injection into surgical sites via a minimally invasive procedure, thereby saving the effort and time of surgeons during surgeries and reducing recovery time of the patients. Moreover, when used as carrier materials for mesenchymal stem cells, the hydrophobic cavities of the β-CD in the HGM hydrogels provide compartments for loading and controlled release of hydrophobic small molecules promoting stem cell differentiations. The hMSCs encapsulated in the HGM hydrogels exhibit enhanced osteogenic differentiation compared to those in the chemically crosslinked hydrogels of the identical material composition under both in vitro and in vivo conditions.

Hydrogels made of biopolymers, such as hyaluronic acid, gelatin, and collagen, are promising for biomedical applications due to their good biocompatibility and intrinsic bioactivities [1, 2, 3, 4]. However, most of these biopolymer-based hydrogels are covalently crosslinked three dimensional networks, which are stable and stiff but brittle and lack self-healing capability [5]. Alternatively, supramolecular hydrogels stabilized by physical crosslinking can possess unique physical properties that are generally not found in chemically crosslinked hydrogels, including self-healing, shear thinning, mechanical resilience, facile formation and modular functionalization [6, 7, 8, 9]. Physical complexations between host and guest molecules are often employed to form supramolecular hydrogels [10, 11, 12]. However, to form these supramolecular hydrogels, chemical modification of the biopolymers is usually required, which may alter the biological and physical properties of the biopolymers [13, 14, 15]. Moreover, the inefficient binding between complementary motifs on the bulky high molecular weight biopolymers due to steric hindrance may also weaken the mechanical properties of the hydrogels. Herein the inventors show the formation of mechanically resilient supramolecular hydrogels, free from chemical modifications and direct crosslinking of the biopolymers, via a novel "Host-guest macromer" (HGM) approach. Briefly, gelatin is first physically coupled to mobile mono-functionalized acrylated β-cyclodextrins (named Ac-β-CD) via the host-guest interaction between the phenylalanine residues of gelatin and the hydrophobic cavities of β-CD to obtain the "Host-guest macromere." Subsequent UV-initiated polymerization of the acrylates produces the HGM supramolecular gelatin hydrogels that are highly stretchable and self-healable. Furthermore, the residual β-CD hydrophobic cavities in the HGM hydrogels afford the potential for modular modifications such as incorporation of hydrophobic drugs and tethering of bioactive molecules. This simple but effective strategy opens up a new route to develop biopolymeric supramolecular hydrogels with enhanced physical and biological functionalities as drug and/or cell carriers for regenerative medicine.

Figure 6:
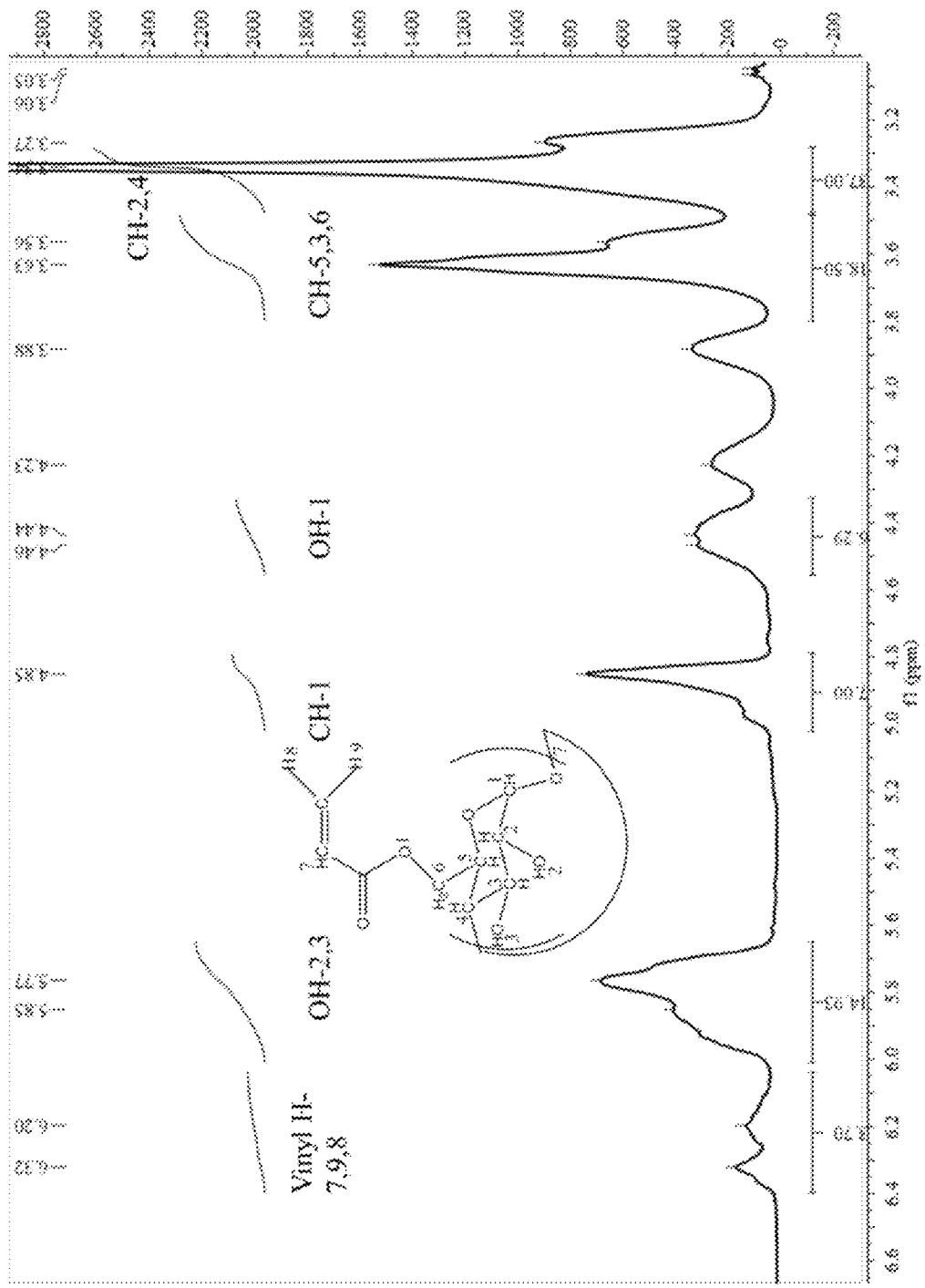
FIG. 6 $^1$H NMR of Ac-β-CD recorded in DMSO-d6.
Figure 7:
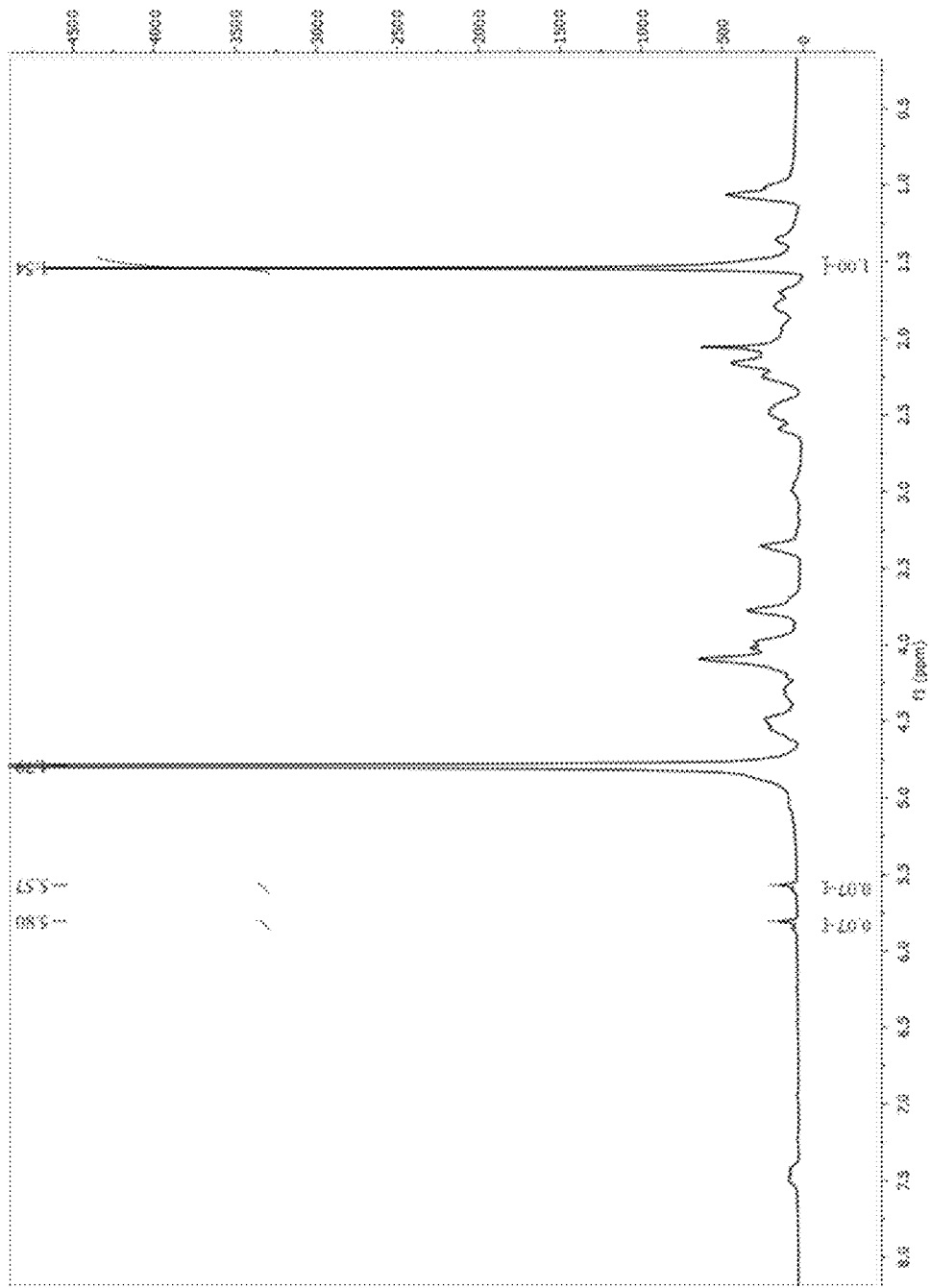
FIG. 7 $^1$H NMR of methacrylated gelatin with DMMA as the internal reference recorded in D2O at 37° C.
Figure 8A:
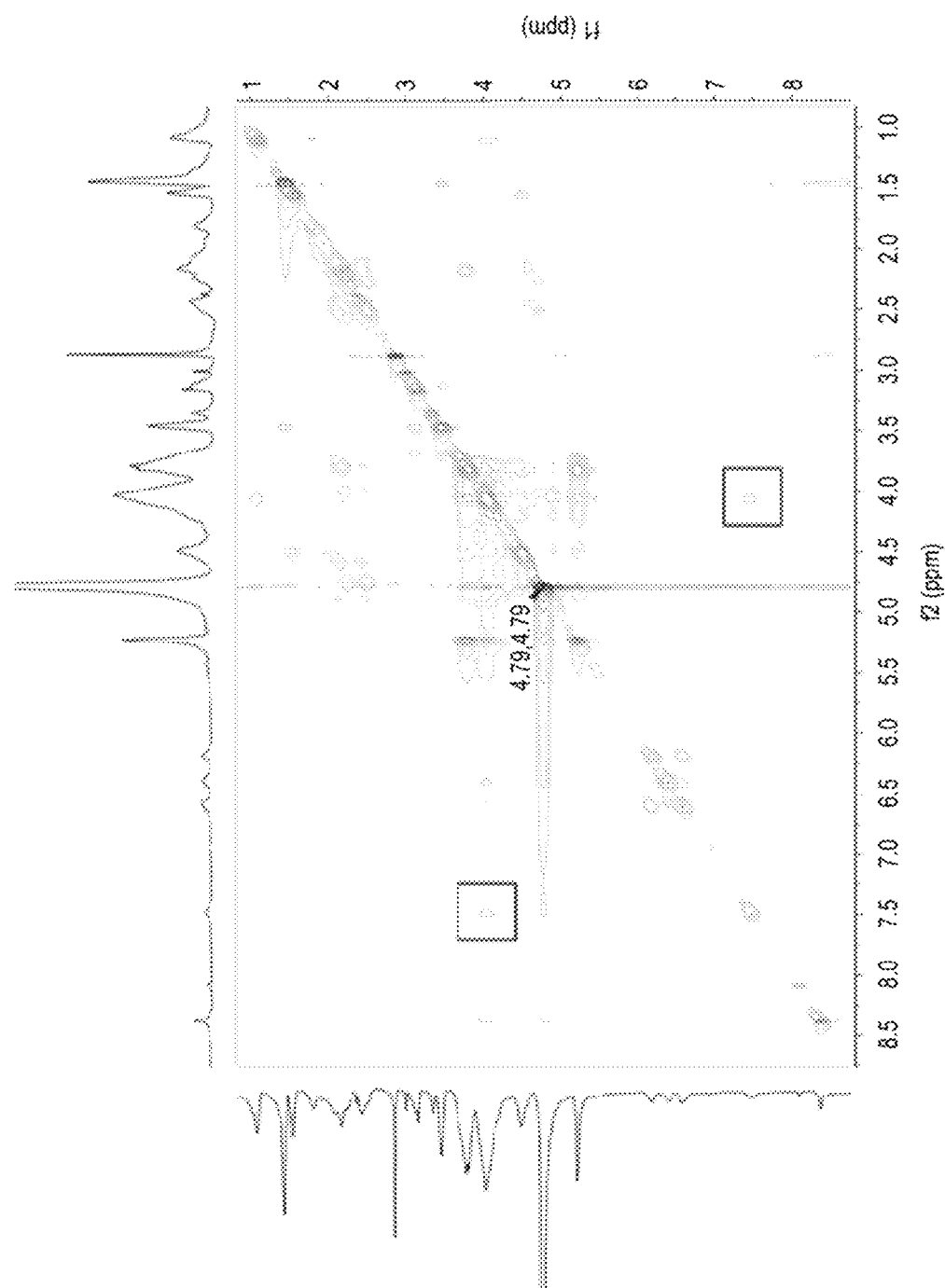
FIGS. 8A-8B The host-guest interaction the phenylalanine residues of gelatin and the hydrophobic cavities of β-CD. 8a, 2D-NOSEY NMR of gelatin/Ac-β-CD mixture recorded in $D_2O$ at 37° C. 8b, Reacted phenylalanine residues percentage dependent on the Ac-β-CD concentration.

HGM Supramolecular Hydrogels Are Formed by Enhanced Host-Guest Complexation Without Chemical Crosslinking β-cyclodextrin, a nontoxic and biocompatible cyclic oligomer of glucose, is widely used host molecule that can complex with various hydrophobic guest molecules including the aromatic moieties along the gelatin polymer chains ($K_a$~100 $M^{-1}$) [16, 17, 18]. The inventors synthesized acrylate-bearing host molecule Ac-β-CD, which can form inclusion complex with the benzene ring of the phenylalanine residues of gelatin. $^1H$ NMR result (FIG. 6) confirms the conjugation of a single acrylate to each β-CD, i.e., mono-functionalization, which is essential to the formation of pure physically crosslinked hydrogels free of chemical crosslinks during the subsequent chain polymerization of the acrylates. According to the $^1H$ NMR analysis with DMMA (FIG. 7) as the internal reference, the phenylalanine residue content is estimated to be 7.26×10$^{-5}$ mole in a gram of gelatin. 2D-NOSEY NMR (FIG. 8) reveals the host-guest interaction between the Ac-β-CD hydrophobic cavities and the phenylalanine residues of gelatin upon mixing. The gelatin molecules coupled with the Ac-β-CD monomers via the host-guest complexation between β-CD and phenylalanine is named as the "Host-Guest Macromer."

The formation of the "Host-Guest Macromer" via the efficient host-guest complexation between the free diffusing Ac-β-CD monomer and the gelatinous benzene ring (phenylalanine) prior to the UV-initiated chain polymerization is essential to the formation and the resulting mechanical properties of the HGM supramolecular hydrogels. Control experiments show that mixing the pre-polymerized Ac-β-CD with gelatin solutions results in no hydrogel formation at 37° C. because the steric hindrance of the bulky polymerized Ac-β-CD chain likely significantly hampers the complexation between the gelatinous benzene ring and Ac-β-CD (FIG. 1). This finding demonstrates that the "Host-Guest Macromer" approach developed in this study significantly enhances the host-guest complexation, leading to the formation of the supramolecular hydrogels with improved mechanical properties, which cannot be achieved by mixing host polymer and guest polymer pairs.

Figure 8B:
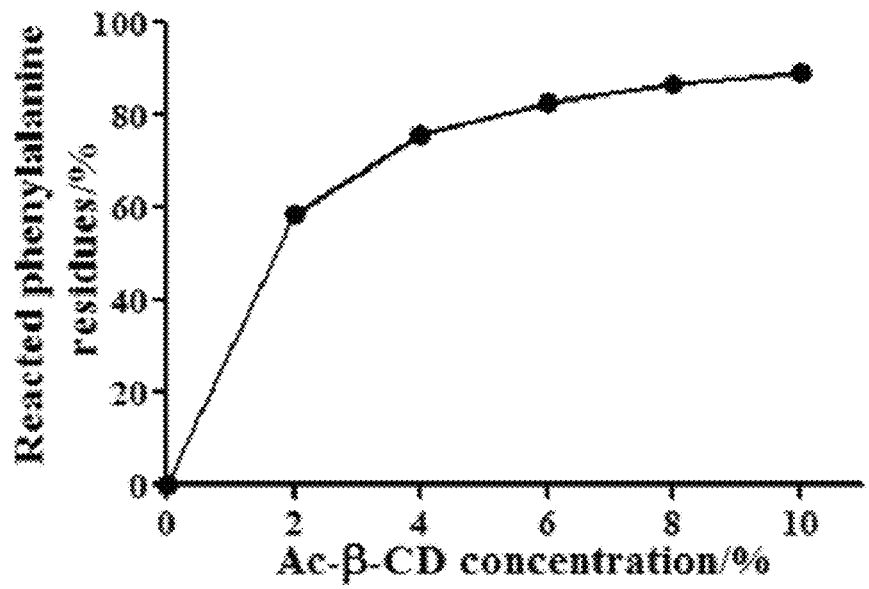

At a constant gelatin concentration of 8% (w/v), the degree of acrylate modification of the gelatin via host-guest interaction depends on the concentration of Ac-β-CD. The HGM hydrogels were prepared using varying Ac-β-CD concentrations after performing theoretical calculation to estimate the modification degree of gelatin by Ac-β-CD (FIG. 8b). At a relatively high concentration of Ac-β-CD (10% (w/v)) that ensures more than 85% of the phenylalanine residues couple to Ac-β-CD (FIG. 8b), UV initiated chain polymerization of the acrylates of the Ac-β-CDs results in the formation of hydrogels. As shown in the qualitative tube inversion tests (FIG. 1), compared to the pure gelatin hydrogels ($Gel_8CD_{10}$, containing 8% (w/v) gelatin only) that melt into solutions at 37° C., HGM hydrogels ($Gel_8CD_{10}$, containing 8% (w/v) gelatin and 10% (w/v) Acβ-CD) are still in the gel state. The melting point of gelatin hydrogel is known to be typically lower than 35° C., depending on the gelatin grade and concentration. Thus, the $Gel_8CD_{10}$ hydrogels at 37° C. should be stabilized by the host-guest interactions between the polymerized Ac-β-CDs and phenylalanine residues of the gelatin. Further confirming this, incubation of a competitive guest, 1-adamantanamine hydrochloride (ADA), results in the disintegration of the $Gel_8CD_{10}$ hydrogels at 37° C. (FIG. 1). ADA binds to β-CD (Ka around 10$^5$ $M^{-1}$) with much higher affinity leading to the dissociation of gelatin/Ac-β-CD complex, and turns the $Gel_8CD_{10}$ hydrogel into a solution state.

Figure 2A:
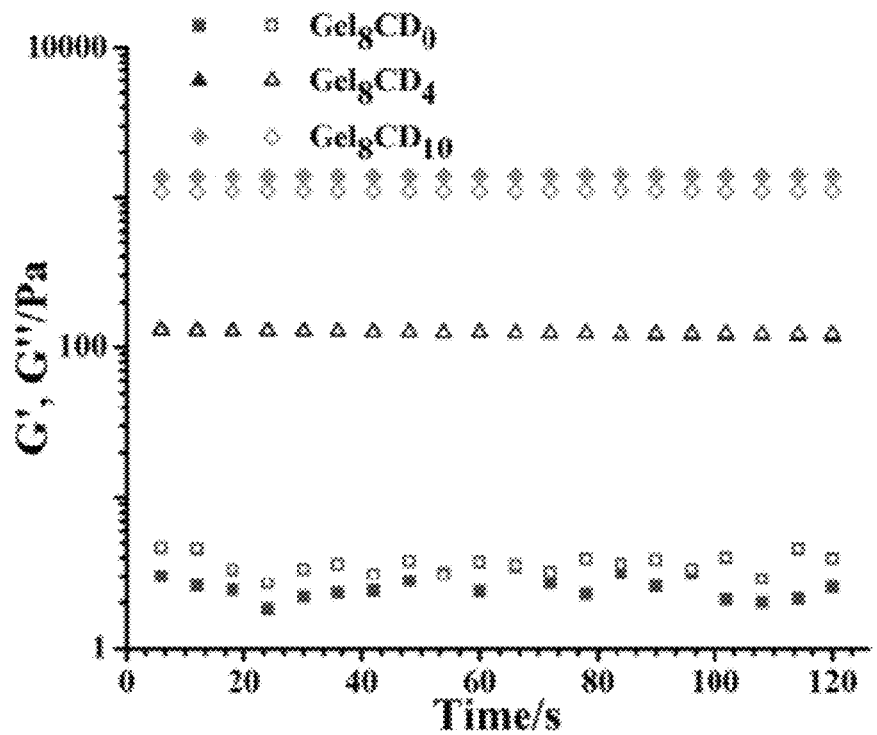
FIGS. 2A-2D Mechanical properties of HGM hydrogels. a, time sweep of dynamic rheology study on $Gel_x$-$CD_y$ at 37° C. b, strain-stress curves of Me-gelatin and $Gel_x$-$CD_y$ at 37° C. c, cyclic tensile testing of $Gel_8$-$CD_{10}$ at 37° C. d, compress test comparison between MeGel and $Gel_8$-$CD_{10}$.
Figure 9A:
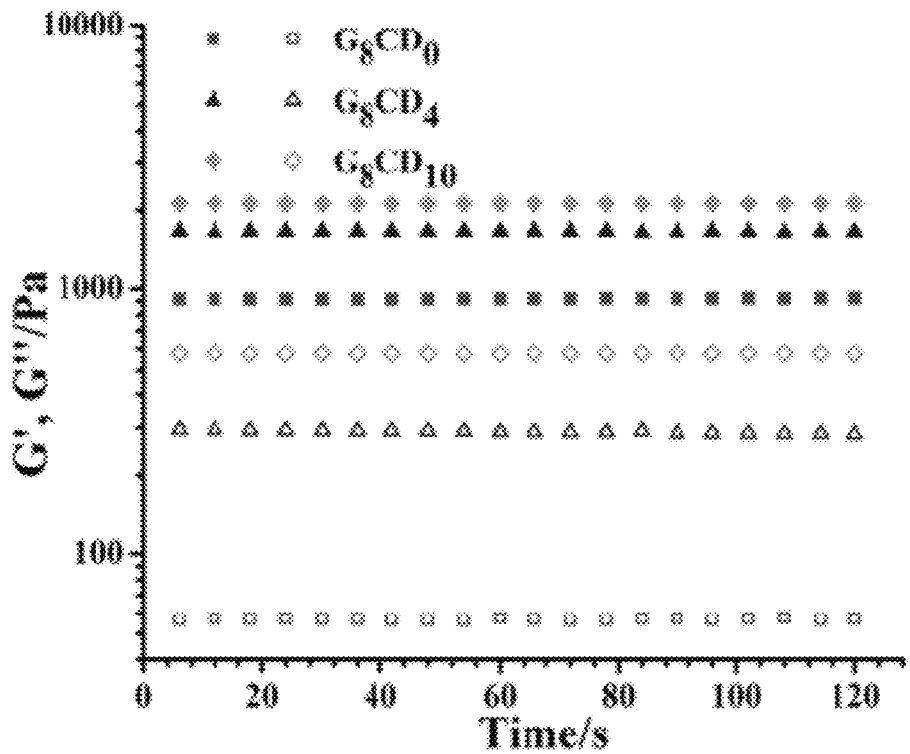
FIGS. 9A-9C Mechanical properties of HGM hydrogels at 25° C.

More quantitative analysis of the hydrogel property was performed by dynamic rheology testing (FIG. 9a, FIG. 2a). As the Ac-β-CD content increases, both the storage and loss modulus of the supramolecular hydrogels increases at 25° C. Moreover, at 37° C., compared to the solution state of the $Gel_8CD_{10}$ pure gelatin hydrogels (the loss modulus being higher than the storage modulus), the $Gel_8CD_4$ and $Gel_8CD_{10}$ hydrogels are both in gel state (the storage modulus being higher than the loss modulus), indicating the importance of the host-guest interactions between gelatin and β-CD to the gelation process.

HGM Hydrogels Are Mechanically Resilient

Figure 2B:
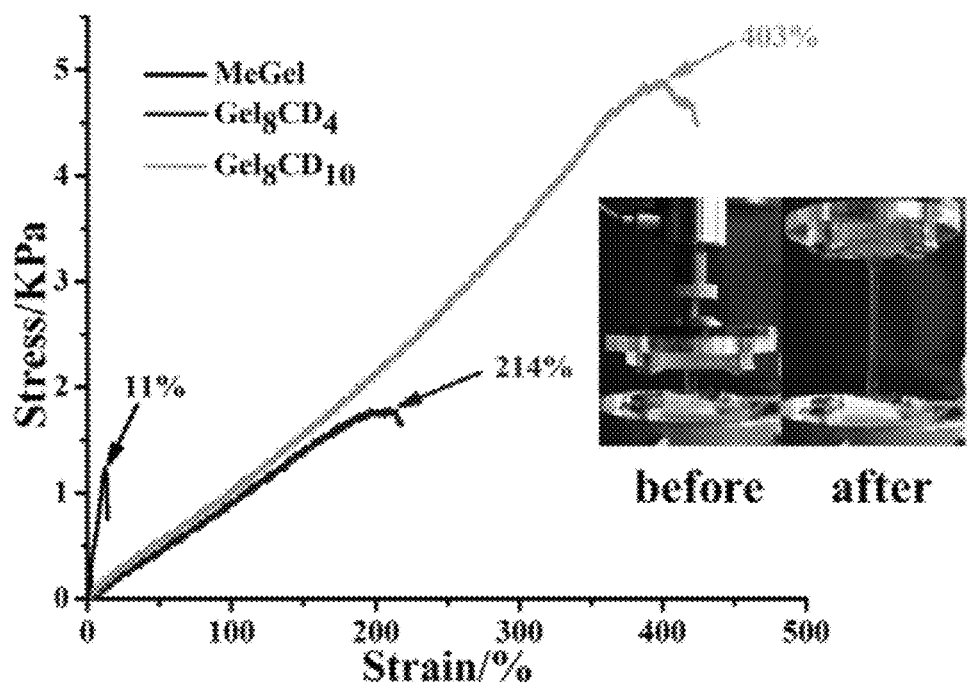
Figure 2C:
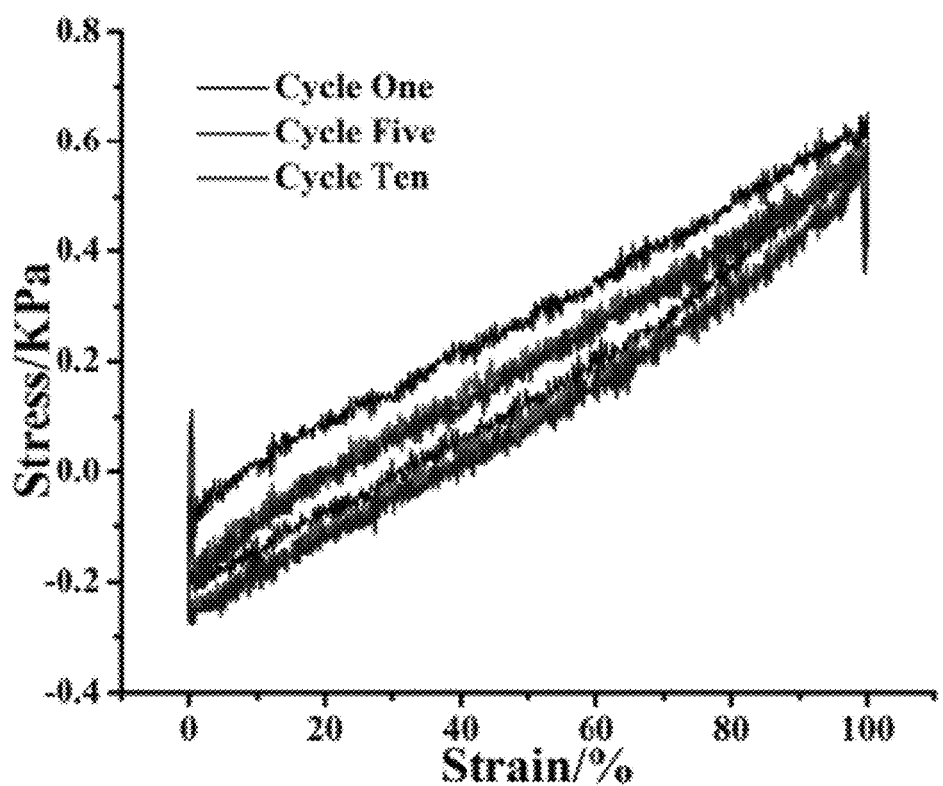
Figure 2D:
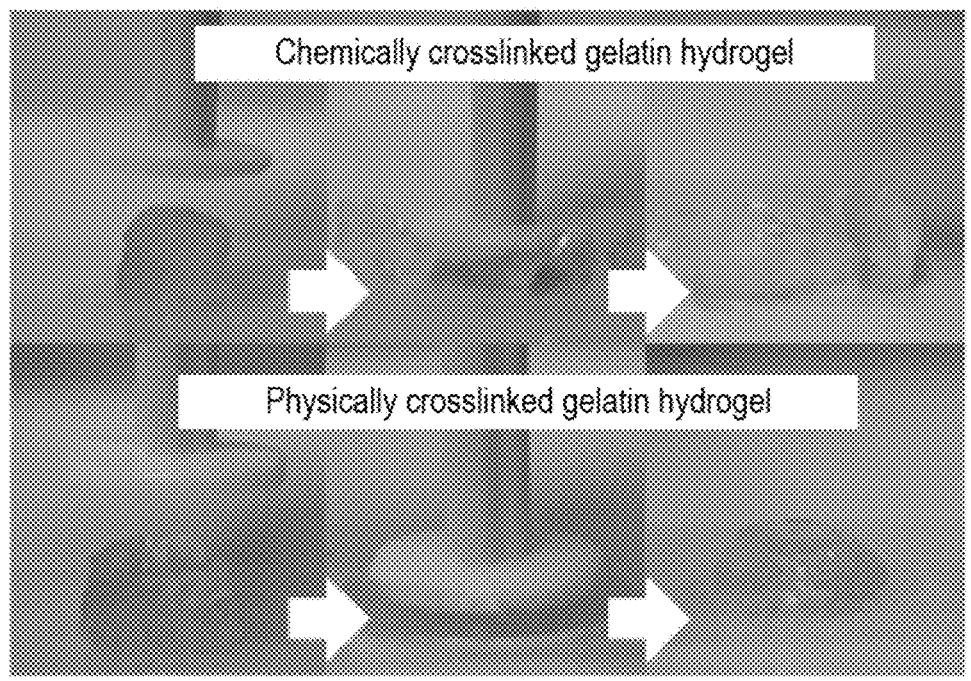
Figure 9B:
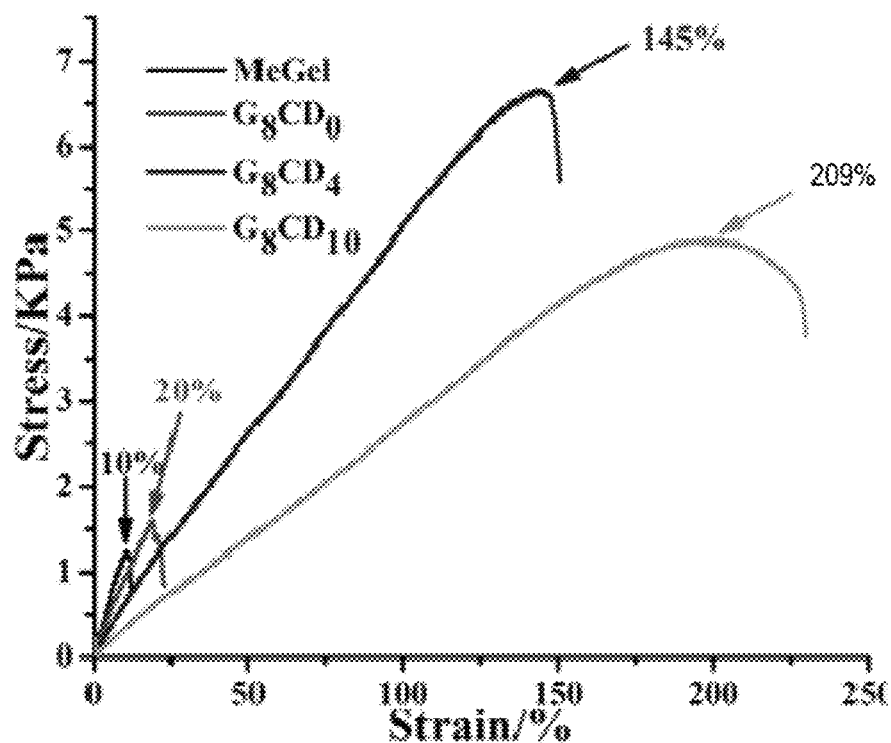
Figure 9C:
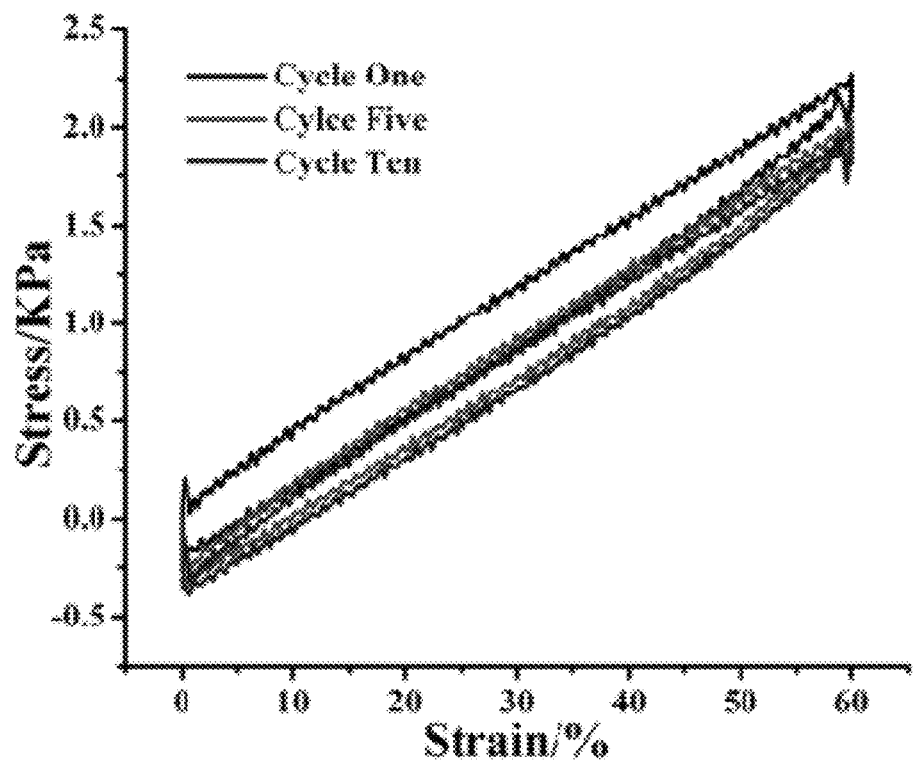

The host-guest interactions between Ac-β-CD and gelatin significantly enhance not only gelatin hydrogel stiffness, as evidenced by the time sweep analysis (FIG. 9a and FIG. 2a), but also the tensile and compress properties (FIG. 9b-c and FIG. 2b-d). At 25° C., unmodified gelatin (8% (w/v), $Gel_8CD_0$) remains as a brittle hydrogel with a small failure strain of around 20% due to inter-molecular interactions (FIG. 9b). Similarly, the chemically crosslinked methacrylated gelatin (MeGel) hydrogels are even more brittle and break at a tensile strain of around 10% at 25° C. (FIG. 9b). In contrast, the physically crosslinked HGM hydrogels containing the same content of gelatin as that in the unmodified gelatin hydrogels, break at much higher strains (145% for $Gel_8CD_4$ and 205% for $Gel_8CD_{10}$) (FIG. 9b). This dramatic change indicates the efficacy of the supramolecular approach in designing highly stretchable hydrogels, in which the reversible guest-host crosslinks play a key and distinct role compared to the conventional chemical crosslinks. It should be noted that the Young's modulus of the HGM hydrogels decreases with the increasing content of Ac-β-CD (FIG. 9b). This may be due to the reduction of gelatin inter-molecular interactions as a result of the hydrophobic phenylalanines complexing with β-CDs. Further confirming this hypothesis, at 37° C. under which gelatin inter-molecular interactions are largely absent, the Young's modulus of the supramolecular gelatin hydrogels shows no difference with varying Ac-β-CD contents (FIG. 2b). Moreover, at 37° C., the breaking strains are higher than those measured at 25° C. The breaking strain of the $Gel_8CD_{10}$ hydrogels reached 400%, nearly 40 times that of the methacrylated gelatin hydrogels (MeGel). Moreover, the HGM hydrogels stabilized by the host-guest interactions are resistant to fatigue under repeated tensile loading and unloading cycles. For instance, the $G_8CD_{10}$ hydrogels exhibit nearly identical elastic property throughout ten cycles of tensile testing (FIG. 2c). At last, comparing the compression behaviors of MeGel with those of the $Gel_8CD_{10}$ hydrogels at 37° C. (FIG. 2d), MeGel hydrogels rupture to pieces, but $Gel_8CD_{10}$ hydrogels can recover to the original shape. The mechanical resilience of the supramolecular hydrogels is critical to the maintenance of the hydrogel integrity in load-bearing locations in vivo such as the hip and knee joints. The $Gel_8CD_{10}$ hydrogels were used due to the excellent mechanical properties (named as "HGM supramolecular gelatin hydrogels", or "HGM hydrogels" in short) for the following experiments.

HGM Hydrogels Are Capable of Self-Healing

Figure 3A:
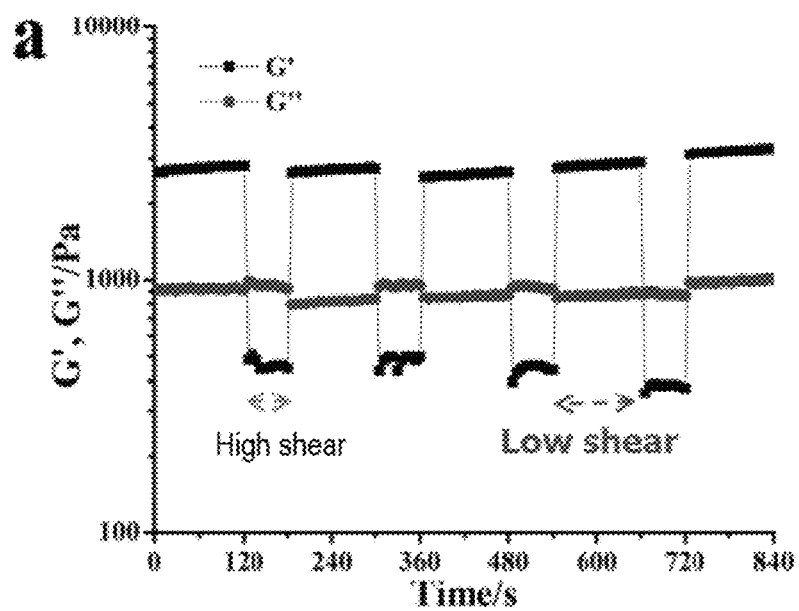
FIGS. 3A-3D The unique features of self-healing, moldability and injectability of the supramolecular gelatin hydrogels not found in chemically crosslinked gelatin hydrogels. 3a, the shear-thinning behavior: the supramolecular hydrogels exhibit sol-gel transition during the switching of high and low shear strain as evidenced by the rheology study. 3b, the self-healing capability: the two halves of the cut supramolecular hydrogel self-heal to reintegrate into one piece after brief incubation in juxtaposition. 3c, moldability and injectability of the supramolecular gelatin hydrogels: i) a square-shaped hydrogel before injection; ii) the hydrogel is sucked into a syringe; iii) the hydrogel is injected into a triangular mold through a G18 needle; iv) the mold is removed after 10 minutes and the hydrogel adopts the shape of the mold. 3d, injectability and adhesiveness to a biological tissue defect: i) a critically-sized cartilage defect in a swine femoral condyle; ii) the injection of the MeGel hydrogel through a G18 needle results in fragmentation of the hydrogel, and poor hydrogel adhesion to the native cartilage is observed; iii) the supramolecular $Gel_8$-$CD_{10}$ hydrogel is injected through the same needle into the defect and adheres to the surrounding native cartilage; iv) mechanical pulling shows that the injected $Gel_8$-$CD_{10}$ hydrogel remains strongly adhesive to the cartilage defect when submerged in Water.
Figure 3B:
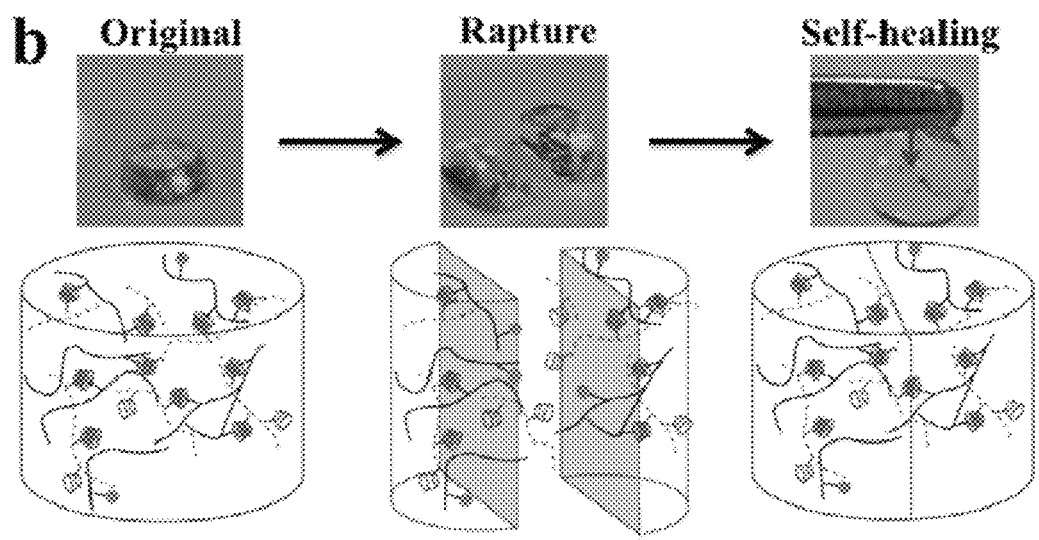
Figure 3C:
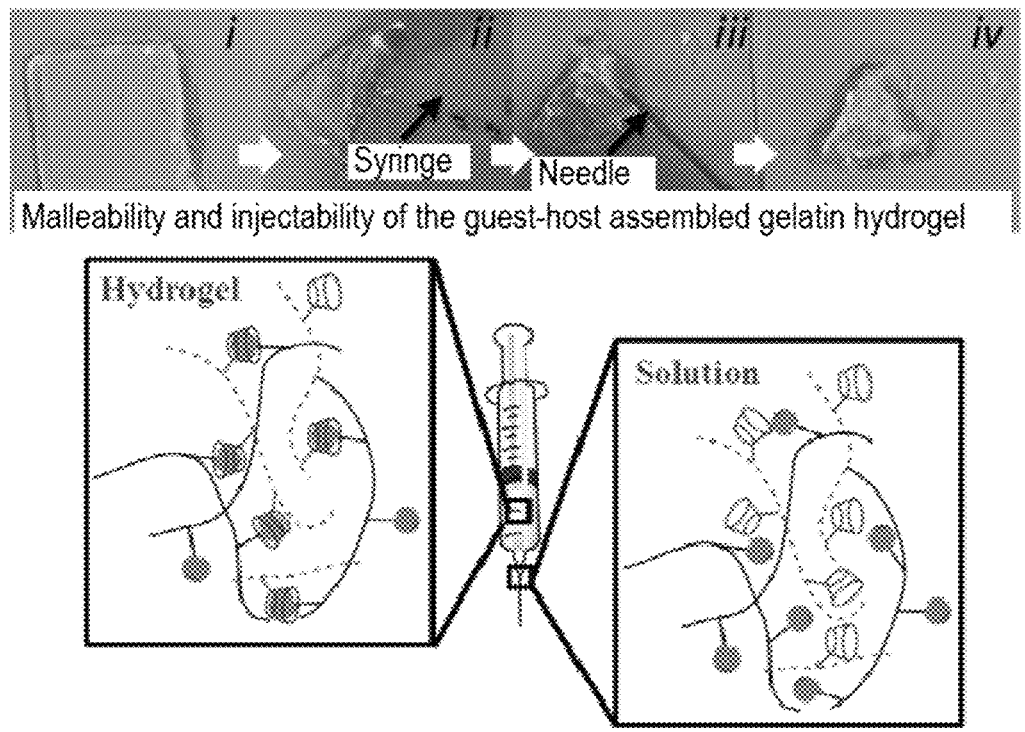

The rheology analysis reveals that our HGM supramolecular gelatin hydrogels ($Gel_8CD_{10}$) exhibit the typical shear thinning behavior. The HGM hydrogels transition into the "sol" state under a high shear strain of around 1000%, but recover to the "gel" state under a subsequent low strain of 1% (FIG. 3a). Moreover, another important feature of the HGM hydrogels is the self-healing ability due to the reversible nature of the physical crosslinking. After being cut into separate pieces, the HGM hydrogels are capable of self-healing and becoming one integrated piece again (FIG. 3b). After 5 minutes of healing, the self-healed hydrogel recovers partial tensile property of the original hydrogels (FIG. 3c). This self-healing capability the HGM hydrogels improves the retention and structural integrity of the hydrogels, and therefore the targeted delivery of the loaded cells/drugs after injection, especially in load-bearing locations in vivo.

Figure 3D:
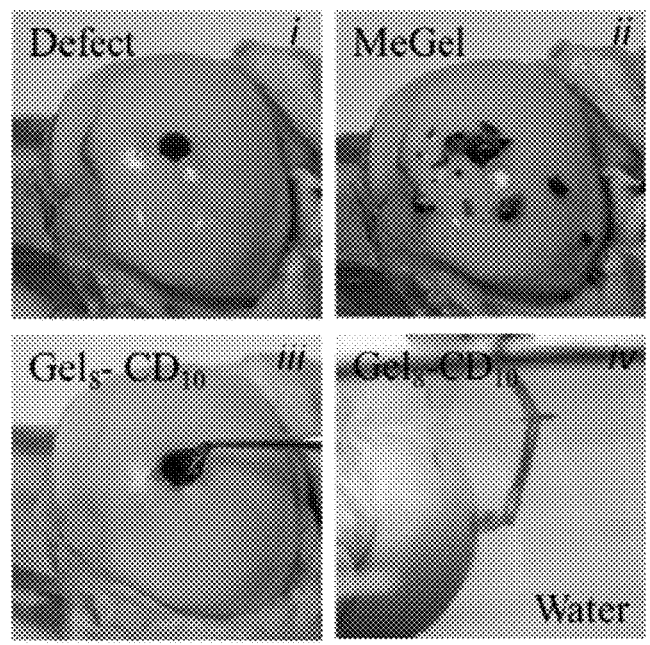

More interestingly, due to the shear thinning property, the preformed HGM supramolecular gelatin hydrogels can be drawn into a syringe and injected through a G18 needle into a mold of different shape (FIG. 3d). The injected HGM hydrogels conform to the mold and retain the shape of the mold after the removal of the mold (FIG. 3d, iv). The conventional injectable hydrogels generally require the preparation of the precursor solutions in the operation theatre and immediate injection to form the hydrogels in situ via either chemical crosslinking or physical interactions (e.g., thermo-responsive hydrogels)[2]. The HGM hydrogels of this invention can be pre-formed with the encapsulated therapeutic cells and drugs first, maintained in the culture condition, and injected into the recipients in the gelation form at a prescribed time later. This "gelation first and injection later" quality of the HGM hydrogels eliminates the steps of preparing the macromer, cells and drugs mixture solutions required immediately before the injection, thereby greatly simplifying the injection procedures to be performed by the surgeons in the operation theatre. Furthermore, the HGM hydrogels regain the "gel" state and conform to the geometry of the injection sites immediately after exiting from the needle tip. This limits the potential loss of the injected materials due to spreading and leakage into unintended locations neighboring the injection sites, thereby enhancing the targeted delivery of the carried therapeutic cargos (cells and drugs).

HGM Hydrogels Are Adhesive to Biological Tissues

To evaluate the ability to integrate with native biological tissues, the MeGel and HGM supramolecular gelatin hydrogels ($Gel_8CD_{10}$) are injected to cartilage defects in swine femur condyles (FIG. 3d). The supramolecular hydrogels strongly adhere to the surrounding native cartilage even under an aqueous condition (FIG. 3d iii, iv), whereas the chemically crosslinked MeGel hydrogels detach easily from the cartilage defects (FIG. 3d ii)). The complexation between the β-CDs in the HGM hydrogels and the native cartilaginous phenylalanines together with potential hydrogen bonding between the hydrogel structures and cartilage matrix components may have contributed to the adhesion between the HGM hydrogels and the native cartilage. This tissue-adhesive property of the HGM hydrogels will effectively assist the post-injection hydrogel retention and seamless integration with the host tissues in vivo, which will facilitate the migration of the endogenous cells into the injected hydrogels through the hydrogel-host tissue interfaces. Remarkably, the supramolecular gelatin hydrogels remain adhesive to soft tissues such as articular cartilage in an aqueous environment, which is often the condition at most of the injection sites of clinical interest.

HGM Hydrogels Facilitate Cell Infiltration and Migration

Figure 4A:
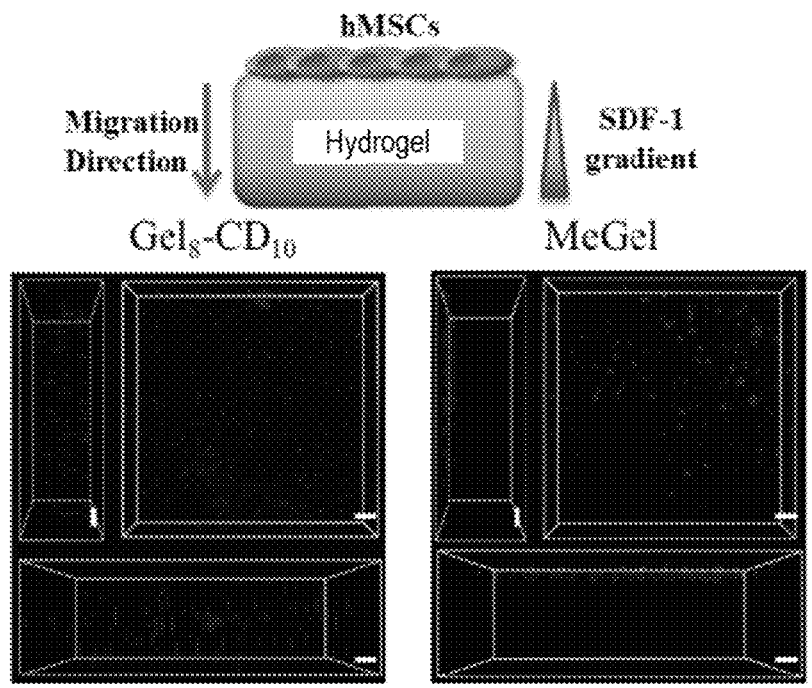

The mobilization of the host endogenous cells including progenitor cells and stem cells is crucial to expediting the healing of tissue injuries[19, 20, 21]. The implant biomaterials that favor cell infiltration and migration will greatly facilitate the recruitment of these endogenous cells to participate in the healing process. The inventors conducted a cell migration assay to assess the infiltration and migrations of hMSCs in the traditional chemically crosslinked MeGel hydrogels and our HGM gelatin hydrogels. As shown in FIG. 4a, the hMSCs seeded the MeGel hydrogels remain largely on top of the hydrogels with few cell infiltrations after 2 hours of exposure to a chemoattractant gradient. In contrast, nearly all the hMSCs seeded on the HGM hydrogels penetrate into and migrate by large distances within the hydrogels under the same condition. Previous studies have shown that stiffer hydrogels actually promote more cell migrations compared to softer hydrogels of the same material[22, 23]. Therefore, the enhanced cell migrations within our supramolecular gelatin hydrogels, which are softer than the MeGel hydrogels, are likely due to the reversible nature of the host-guest complexation crosslinks in the supramolecular hydrogels. It is postulated that the encapsulated hMSCs are capable of "breaking" the crosslinks in the HGM hydrogels via cell traction forces to find a way for migration. After the passage of the cells, the disconnected host and guest molecules in the HGM hydrogels are able to reestablish the crosslink by complexation with each other again. Therefore, the HGM hydrogels facilitate cell infiltration and migration without suffering structural damage.

Figure 4B:
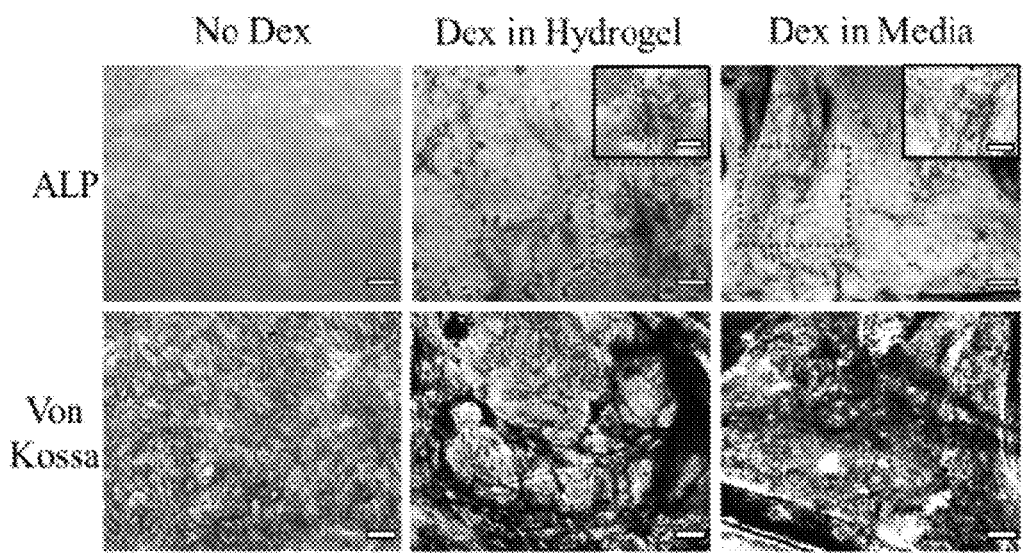

HGM Hydrogels Enable Controlled Release of Hydrophobic Small Molecules and Support HMSC Differentiation in Vitro Alkaline phosphatase (ALP) is an early osteogenesis marker protein and an essential enzyme for ossification. ALP staining reveals little ALP activity in the hMSCs cultured on the HGM hydrogels with no Dex supplementation (No Dex, negative control) (FIG. 4b). In contrast, considerable ALP staining is found in the group for which a bolus dose of Dex is encapsulated in the HGM hydrogels during hydrogel fabrication without supplementation of Dex in media (Dex in Hydrogel) (FIG. 4b). The staining intensity of the "Dex in Hydrogel" group is similar to that of the group for which Dex is supplemented continuously in the media (Dex in Media) (FIG. 4b). Von Kossa staining further reveals the substantial mineralization in the hydrogels loaded with Dex (Dex in Hydrogel), and the amount of mineralization is comparable to the group that receives continuous media supplementation of Dex (Dex in Media) (FIG. 4b). β-CD, which complexes with hydrophobic molecules via its hydrophogic cavity, has long been used in the pharmaceutical industry to improve the solubility and bioavailability of hydrophobic drugs[18, 24]. The hydrophobic cavities of the β-CDs in the HGM hydrogels not only help retain Dex in the hydrogels but also enable long term controlled release of the Dex to the encapsulated hMSCs. This unique feature makes the HGM hydrogels an ideal material for the delivery of stem cells together with differentiation-inducing drugs to tissue defects in vivo, where the continuous addition of the drugs is difficult to implement.

Figure 5A:
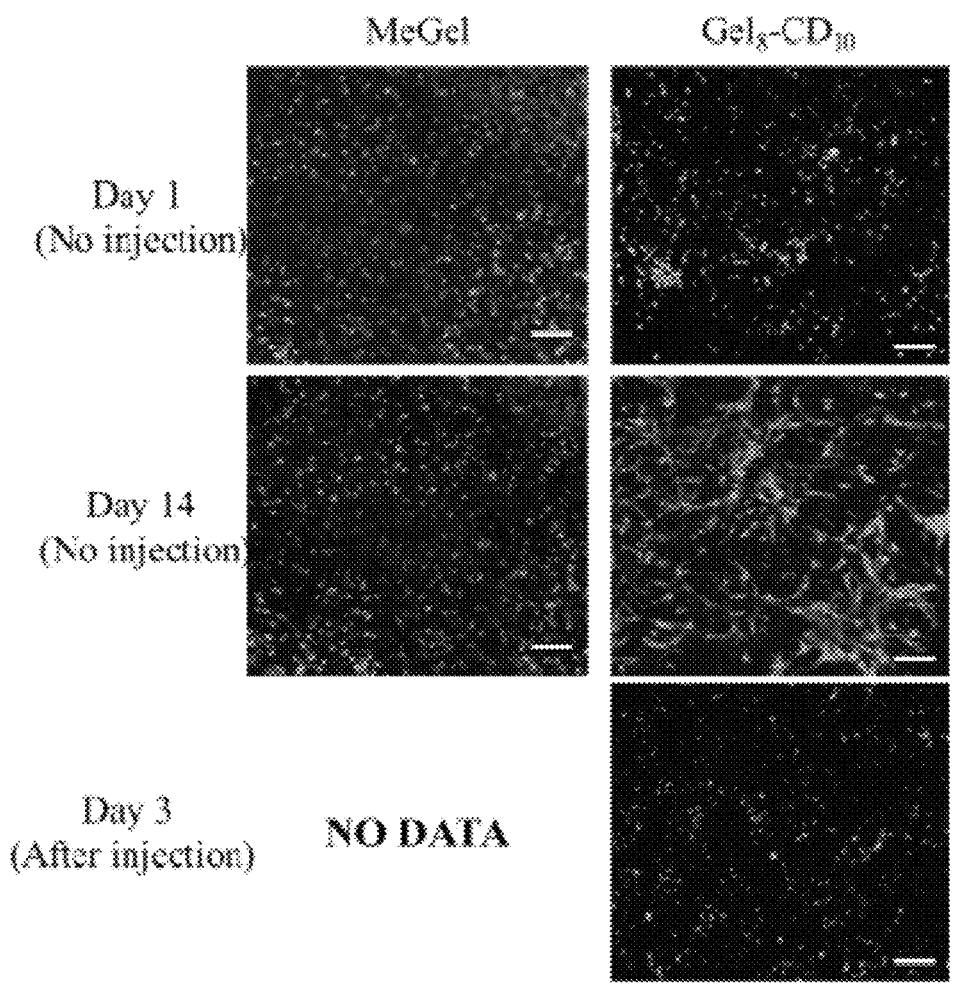
Figures 5B, 5C:
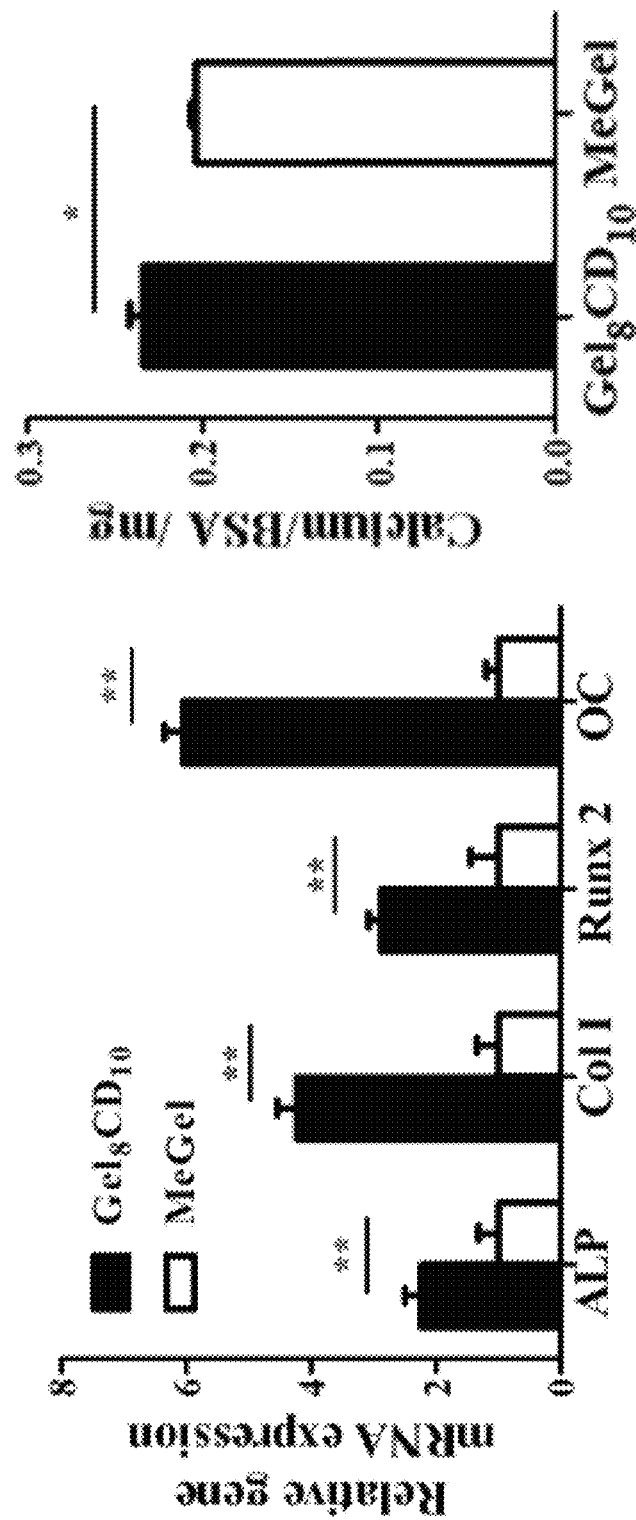
Figure 5D:
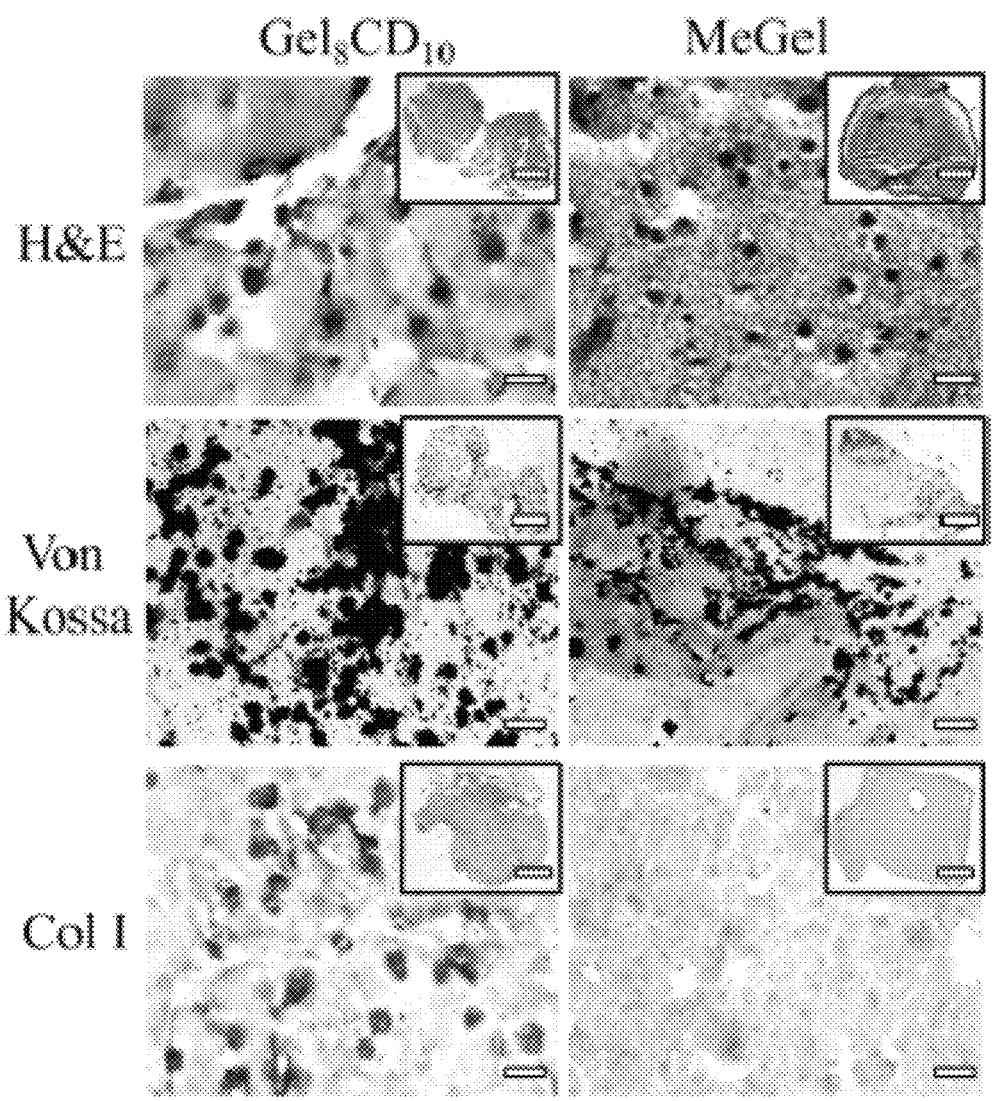

For 3D in vitro and in vivo culture, 1% (w/v) PEGDA is added during the fabrication of the hMSC-laden HGM supramolecular gelatin hydrogels in order to prolong the stability of the HGM hydrogels for long term culture. The addition of the PEGDA at this low concentration does not significantly alter the unique features of the HGM hydrogels as described above. Viability staining indicates that the majority (>95%) of the encapsulated hMSCs are alive in the HGM hydrogels after 14 days of culture in osteogenic media, similar to the cell viability in the MeGel hydrogels (FIG. 5a). Strikingly, the hMSCs encapsulated in the HGM hydrogels spread substantially in size and adopt a stellate morphology after 14 days of culture, whereas the hMSCs in the MeGel hydrogels remain in the initial rounded morphology (FIG. 5a). The hematoxylin and eosin stain (H&E) staining further verifies the drastic change in cell morphology in the HGM hydrogels with increasing culture time (FIG. 5d). This finding confirms the hypothesis that the cells encapsulated in the HGM hydrogels are able to remodel the surrounding hydrogel structures, likely by cell traction forces, due to the reversible crosslinking in the HGM hydrogels. To test the feasibility of injecting cell-laden hydrogels, hMSC-laden HGM hydrogels are injected through a G18 needle after one day of culture and cultured for another two days before viability staining. The hMSCs encapsulated in the HGM hydrogels remain largely viable after the injection. This finding demonstrates the feasibility of the HGM hydrogels of the present invention as an injectable carrier material for the delivery of therapeutic cells including stem cells into patients' internal sites of clinical interests.

Figure 10:
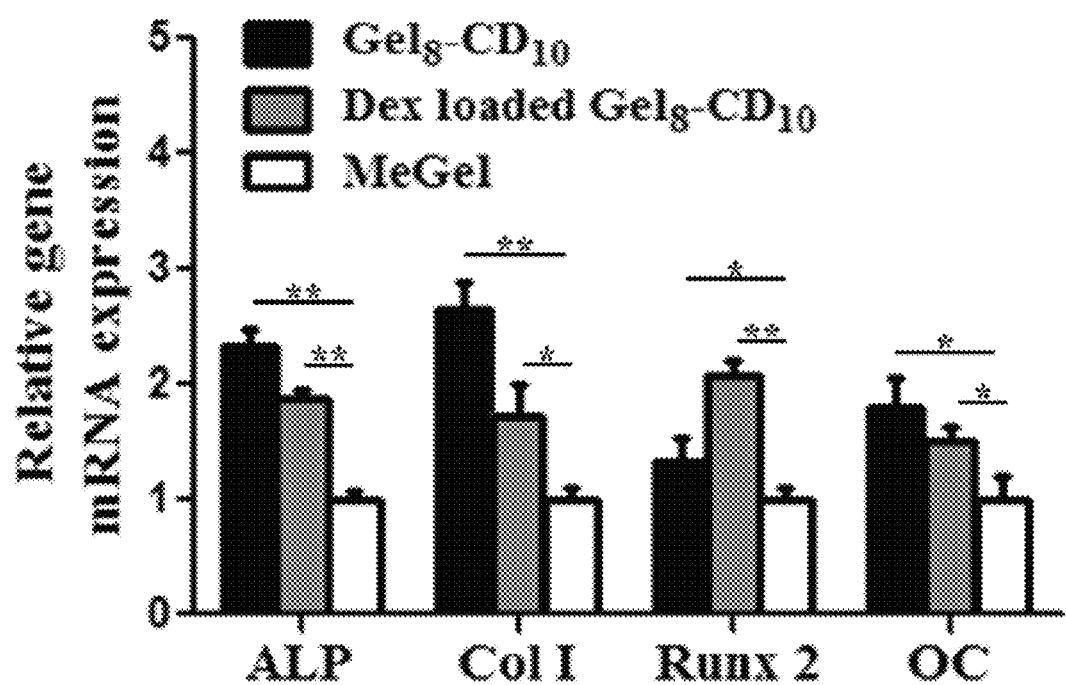
FIG. 10 Gene expression (normalized to GAPDH) of selected osteogenic markers (alkaline phosphatase (ALP), type collagen I (Col I), runt-related transcription factor 2 (Runx2), and osteocalcin (OC)) of hMSC-laden HGM and MeGel hydrogels after 14 days of osteogenic culture.

To evaluate the differentiation of hMSCs encapsulated in the HGM gelatin supramolecular hydrogels, the hMSC-laden HGM hydrogels were cultured in the osteogenic media. After 14 days of culture, the hMSCs encapsulated in the HGM hydrogels exhibit significant upregulated expression of osteogenic marker genes including Runx2, type I collagen, ALP and osteocalcin compared to those in the chemically crosslinked MeGel hydrogels (FIG. 5b). Consistent with the gene expression data, the calcium and the type I collagen content, two important markers for osteogenesis, are also higher in the HGM hydrogels than in the MeGel hydrogels. As described above the HGM hydrogels favor cell spreading, and therefore the development of the cell cytoskeletal tension, which has been shown to promote osteogenesis of hMSCs[25, 26]. The hMSC-laden HGM gelatin hydrogels, which are loaded with a bolus dose of Dex during hydrogel fabrication and cultured in Dex-free media (HGM-Dex in Hydrogel), show similar expression level of the osteogenic marker genes as those HGM hydrogels cultured with fresh Dex supplementation after each media change (HGM-Dex in Media). Both these two groups have significantly higher osteogenic gene expressions than the hMSC-laden MeGel hydrogels receiving continuous Dex supplementation (FIG. 10). This finding demonstrates the efficacy of the HGM gelatin supramolecular hydrogels as a carrier material for supporting the differentiation of the encapsulated hMSCs.

HGM Hydrogels Support HMSC Differentiation in Vivo

Figure 5E:
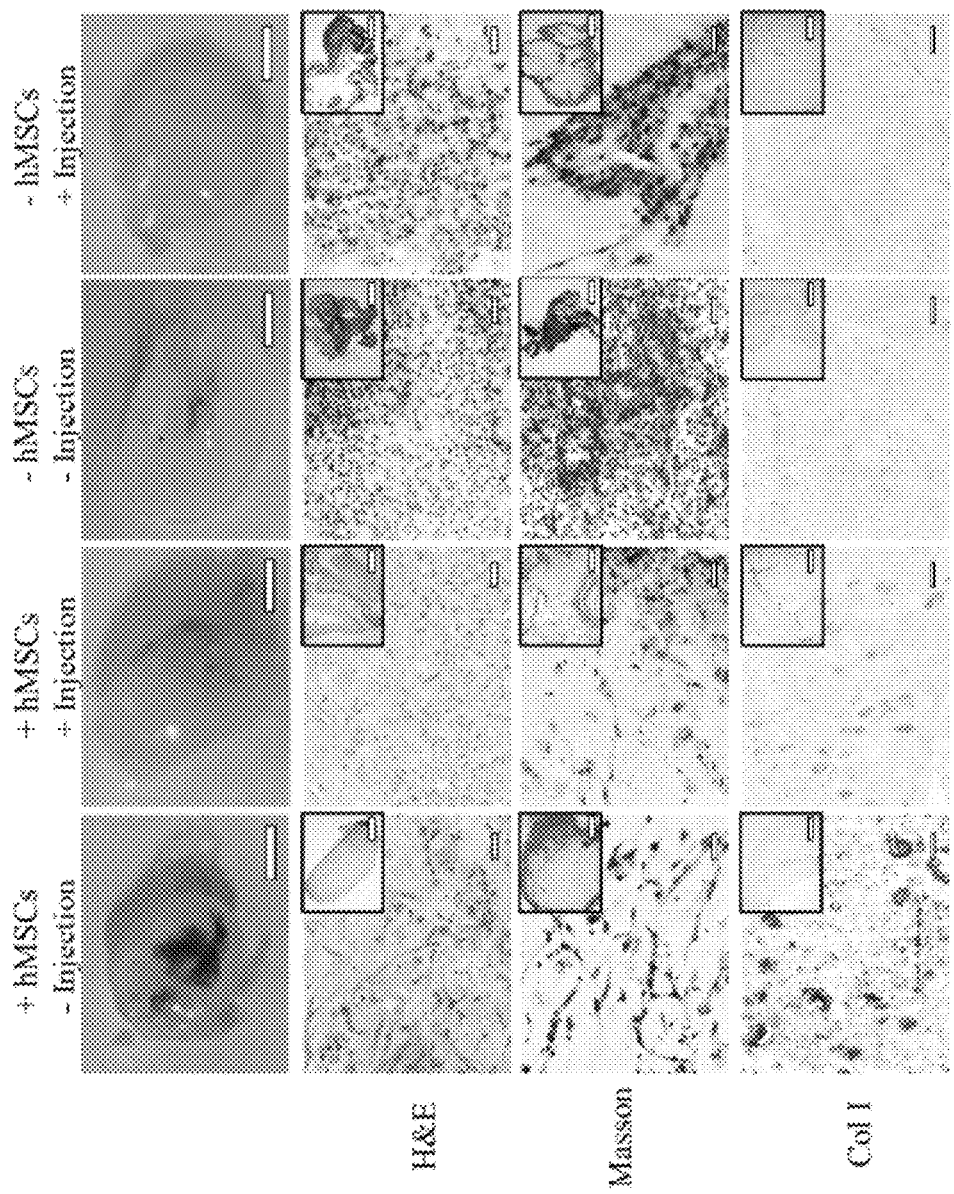

To study the stability the HGM gelatin supramolecular hydrogels in vivo, the inventors directly inserted or injected via a needle Dex loaded HGM hydrogels (with or without hMSCs) into the subcutaneous pockets of nude mices. The pictures of the harvested hydrogels after 14 days of implantation show that both the directly inserted and injected HGM hydrogels remain largely intact (FIG. 5e). The H&E staining and Masson trichrome staining shows that the encapsulated hMSCs spread and deposit type I collagen in both the inserted and injected HGM hydrogels (FIG. 5e). Many cells that appear different from the hMSCs are also found in these implanted HGM hydrogels, especially those hydrogels implanted without hMSCs. These cells are likely endogenous murine cells that originate from the surrounding host tissues. This finding further corroborates the result of the in vitro cell migration study performed by the inventors that the HGM hydrogels allow infiltration and migration of endogenous cells. This unique feature of the HGM hydrogels can potentially greatly simplify the regenerative medicine strategy by eliminating the need of exogenous cells, and help expedite the clinical translation of such therapies[20].

Experimental Procedures

Methods $^1$H NMR of Ac-β-CD was recorded in DMSO-d6 with a Bruker Advance 400 MHz spectrometer at room temperature. $^1$H NMR of methacrylated gelatin was recorded in $D_2O$ with the same equipment at 37° C. Nuclear overhauser effect spectroscopy (NOESY) of gelatin/Ac-β-CD mixture and gelatin/Ac-β-CD/adamantane mixture were performed in $D_2O$ with a Bruker Advance 400 MHz spectrometer at 37° C.

Dynamic oscillatory time, frequency and strain sweeps were performed on an Anton Paar MCR301 rheometer with 25 mm diameter plates (plate to plate) at a 0.2 mm gap size. The hydrogels were homogeneously distributed within the top and bottom plates of the rheometer. Time sweeps were recorded at a strain of 0.1% and a frequency of 10 Hz. Frequency sweeps (0.01-100 Hz) were tested at a fixed strain of 0.1%. Strain sweeps were performed from 10 to 6000% at 25° C. and from 0.1 to 100% at 37° C. at a constant frequency of 10 Hz. For shear recovery test, the sample underwent sequential shear with strain of 0.1% (for 120 s) and 1000% (for 60 s) for 4 cycles, and the recovery of storage (G') and loss modulus (G") were monitored by time sweeps at fixed frequency (10 Hz).

Tension test were done on samples of 5×2×10 mm$^3$ at an extension speed of 1 mm/s using a MACH-1 Micromechanical System. Tensile fatigue test was done with a tensile strain of 60% (at 25° C.) or 100% (at 37° C.) for 10 cycles at the same load speed. For compression test, cylindrical samples (3.5 mm diameter, 3 mm height) were used. Compression fatigue property of the samples was examined at a compression speed of 0.3 mm/s and compressive strain of 60% for 10 cycles.

Migration test was done by using the 24-well transwells. HGM and MeGel hydrogels were formed on the top of the transwells' membrane and put them into a 2-well plate. Then, 100 μl hMSC suspension media (2×10$^6$/ml) were added on the top of the hydrogels and 770 ul growth media with 10 ng/ml SDF-1 into the 24-well plates. After 2 h incubating, the hydrogels were fixed by 4% paraformaldehyde and stained by DAPI.

ALP staining and Von Kossa staining were done on 2D cell culture samples by using fast blue RR salt and 5% sliver nitrate, respectively. Viability was tested on 3D cell culture samples by calcein AM (Live) and ethidium bromide (Dead).

All patents, patent applications, and other publications, including GenBank Accession Numbers, cited in this application are incorporated by reference in the entirety for all purposes.

REFERENCES

1. Seliktar D. Designing cell-compatible hydrogels for biomedical applications. *Science* 2012, 336(6085): 1124-1128.
2. Thiele J, Ma Y, Bruekers S M, Ma S, Huck W T. 25th anniversary article: Designer hydrogels for cell cultures: a materials selection guide. *Adv Mater* 2014, 26(1): 125-147.
3. Van Vlierberghe S, Dubruel P, Schacht E. Biopolymer-Based Hydrogels As Scaffolds for Tissue Engineering Applications: A Review. *Biomacromolecules* 2011, 12(5): 1387-1408.
4. Burdick J A, Prestwich G D. Hyaluronic acid hydrogels for biomedical applications. *Adv Mater* 2011, 23(12): H41-56.
5. Peppas N A, Huang Y, Torres-Lugo M, Ward J H, Zhang J. Physicochemical foundations and structural design of hydrogels in medicine and biology. *Annu Rev Biomed Eng* 2000, 2: 9-29.
6. Appel E A, del Barrio J, Loh X J, Scherman O A. Supramolecular polymeric hydrogels. *Chemical Society reviews* 2012, 41(18): 6195-6214.
Rodell C B, Kaminski A L, Burdick J A. Rational design of network properties in guest-host assembled and shear-thinning hyaluronic acid hydrogels. Biomacromolecules 2013, 14(11): 4125-4134.
8. Park K M, Yang J A, Jung H, Yeom J, Park J S, Park K H, et al. In situ supramolecular assembly and modular modification of hyaluronic acid hydrogels for 3D cellular engineering. *ACS nano* 2012, 6(4): 2960-2968.
9. Jung H, Park J S, Yeom J, Selvapalam N, Park K M, Oh K, et al. 3D tissue engineered supramolecular hydrogels for controlled chondrogenesis of human mesenchymal stem cells. *Biomacromolecules* 2014, 15(3): 707-714.
10. Liao X, Chen Jiang M. Hydrogels locked by molecular recognition aiming at responsiveness and functionality. *Polymer Chemistry* 2013, 4(6): 1733-1745.
11. Li J. Self-assembled supramolecular hydrogels based on polymer-cyclodextrin inclusion complexes for drug delivery. *NPG Asia Mater* 2010, 2: 112-118.
12. Harada A, Kobayashi R, Takashima Y, Hashidzume A, Yamaguchi H. Macroscopic self-assembly through molecular recognition. *Nat Chem* 2011, 3(1): 34-37.
13. Prestwich G D. Hyaluronic acid-based clinical biomaterials derived for cell and molecule delivery in regenerative medicine. *J Control Release* 2011, 155(2): 193-199.
14. Lai J Y. Corneal Stromal Cell Growth on Gelatin/Chondroitin Sulfate Scaffolds Modified at Different NHS/EDC Molar Ratios. *International journal of molecular sciences* 2013, 14(1): 2036-2055.
15. Bigi A, Cojazzi Panzavolta S, Rubini K, Roveri N. Mechanical and thermal properties of gelatin films at different degrees of glutaraldehyde crosslinking. *Biomaterials* 2001, 22(8): 763-768.
16. Bernert D B, Isenbügel K, Ritter H. Synthesis of a Novel Gelatin Glycopeptide by Polymeranalogous Reaction of Gelatin with Mono-6-para-toluenesulfonyl-β-cyclodextrin and its Supramolecular Properties. *Macromolecular rapid communications* 2011, 32(4): 397-403.
17. Rekharsky M V, Inoue Y. Complexation Thermodynamics of Cyclodextrins. *Chemical reviews* 1998, 98(5): 1875-1918.
18. Davis M E, Brewster M E. Cyclodextrin-based pharmaceutics: past, present and future. *Nature reviews Drug discovery* 2004, 3(12): 1023-1035.
19. Chen F M, Wu L A, Zhang M, Zhang R, Sun H H. Homing of endogenous stem/progenitor cells for in situ tissue regeneration: Promises, strategies, and translational perspectives. *Biomaterials* 2011, 32(12): 3189-3209.
20. Burdick J A, Mauck R L, Gorman J H, 3rd, Gorman R C. Acellular biomaterials: an evolving alternative to cell-based therapies. *Sci Transl Med* 2013, 5(176): 176ps174.
21. Ko I K, Lee S J, Atala A, Yoo J J. In situ tissue regeneration through host stem cell recruitment. Exp Mol Med 2013, 45: e57.
22. Ng M R, Besser A, Danuser Brugge J S. Substrate stiffness regulates cadherin-dependent collective migration through myosin-II contractility. *J Cell Biol* 2012, 199(3): 545-563.
23. Ulrich T A, de Juan Pardo E M, Kumar S. The mechanical rigidity of the extracellular matrix regulates the structure, motility, and proliferation of glioma cells. *Cancer Res* 2009, 69(10): 4167-4174.
24. Uekama K, Hirayama F, Irie T. Cyclodextrin Drug Carrier Systems. *Chemical reviews* 1998, 98(5): 2045-2076.
25. McBeath R, Pirone D M, Nelson C M, Bhadriraju K, Chen C S. Cell shape, cytoskeletal tension, and RhoA regulate stem cell lineage commitment. *Dev Cell* 2004, 6(4): 483-495.
26. Khetan S, Guvendiren M, Legant W R, Cohen D M, Chen C S, Burdick J A. Degradation-mediated cellular traction directs stem cell fate in covalently crosslinked three-dimensional hydrogels. *Nat Mater* 2013, 12(5): 458-465.

What is claimed is:

1. A method of producing a hydrogel, comprising the steps of:
   (1) complexing a host molecule and a guest molecule, wherein the host molecule presents a hydrophobic pocket and comprises a monomer component, and wherein the host molecule and guest molecule form a physical interaction between the hydrophobic pocket and a benzene ring of the guest molecule; and
   (2) polymerizing the monomer components to form a cross-linked mesh of the host molecules and guest molecules.

2. The method of claim 1, wherein the host molecule is an acrylated β-cyclodextrin.

3. The method of claim 1, wherein the monomer component is an acrylate.

4. The method of claim 1, wherein the guest molecule is a gelatin, which is not chemically modified.

5. The method of claim 1, wherein the polymerization is initiated by UV radiation.

6. The method of claim 1, wherein the host molecule and the guest molecule are placed in an aqueous solution together.

7. The method of claim 1, wherein at least one additional molecule is present in step (1) when the host molecule and the guest molecule are complexed.

8. The method of claim 7, wherein the at least one additional molecule is a pharmaceutically active ingredient.

9. The method of claim 1, wherein the host molecule is a mono-acrylated β-cyclodextrin and the guest molecule is a gelatin, which is not chemically modified.

10. A hydrogel comprising a cross-linked mesh of a host molecule and a guest molecule, wherein the host molecule presents a hydrophobic pocket and comprises a monomer component, the host molecule and guest molecule forming a physical interaction between the hydrophobic pocket and a benzene ring of the guest molecule, and wherein the monomer components are polymerized to form the cross-linked mesh.

11. The hydrogel of claim 10, wherein the host molecule is an acrylated β-cyclodextrin.

12. The hydrogel of claim 10, wherein the monomer component is an acrylate.

13. The hydrogel of claim 10, wherein the guest molecule is a gelatin, which is not chemically modified.

14. The hydrogel of claim 10, wherein the host molecule is a mono-acrylated β-cyclodextrin and the guest molecule is a gelatin, which is not chemically modified.

15. The hydrogel of claim 10, which is generated by the method of claim 1.

16. The hydrogel of claim 10, formulated in an injectable form.

17. The hydrogel of claim 10, further comprising at least one additional molecule.

18. The hydrogel of claim 17, wherein the at least one additional molecule is a pharmaceutically active ingredient.

19. The hydrogel of claim 10, further comprising a live cell.

20. The hydrogel of claim 19, wherein the live cell is a live stem cell.

21. A method for delivering of a pharmaceutically active ingredient, comprising administrating to a patient the hydrogel of claim 18.

22. A method for promoting cell proliferation or differentiation, comprising the step of administering to a patient the hydrogel of claim 20.

23. The method of claim 22, wherein the hydrogel is applied to a wound site in the patient's body.

24. The method of claim 22, wherein the hydrogel is applied to a surgical wound immediately after a surgical procedure is performed on a patient's body.

* * * * *